(12) United States Patent
Baudin et al.

(10) Patent No.: US 6,693,141 B2
(45) Date of Patent: Feb. 17, 2004

(54) SURFACE-ACTIVE PHOTOINITIATORS

(75) Inventors: Gisèle Baudin, Allschwil (CH); Tunja Jung, Inzlingen (DE)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 33 days.

(21) Appl. No.: 10/026,238

(22) Filed: Dec. 21, 2001

(65) Prior Publication Data

US 2002/0107297 A1 Aug. 8, 2002

Related U.S. Application Data

(62) Division of application No. 09/618,821, filed on Jul. 18, 2000, now Pat. No. 6,376,568.

(30) Foreign Application Priority Data

Jul. 29, 1999 (CH) .............................................. 1398/99

(51) Int. Cl.[7] .............................. C08F 2/50; C08F 4/16
(52) U.S. Cl. ........................ 522/34; 522/35; 522/39; 522/42; 522/44; 522/96; 522/117; 522/126; 522/135; 522/137; 526/194
(58) Field of Search .......................... 522/6, 7, 35, 905, 522/33, 182, 40, 41, 42, 43, 44, 184, 34, 39, 96, 117, 126, 135, 137; 526/194; 525/479; 428/447

(56) References Cited

U.S. PATENT DOCUMENTS

| | | | |
|---|---|---|---|
| 4,391,963 A | 7/1983 | Shirahata ..................... | 528/37 |
| 4,477,326 A | 10/1984 | Lin ........................ | 204/159.13 |
| 4,507,187 A | 3/1985 | Jacobine et al. ........ | 204/159.13 |
| 4,534,838 A | 8/1985 | Lin et al. ................ | 204/159.13 |
| 4,536,265 A | 8/1985 | Fabrizio et al. ........ | 204/159.13 |
| 4,559,371 A | 12/1985 | Hüsler et al. ............... | 204/158 |
| 4,569,953 A | 2/1986 | West et al. .................... | 522/6 |
| 4,587,276 A | 5/1986 | Lien et al. ................... | 522/34 |
| 4,666,953 A | 5/1987 | Klemarczyk et al. ......... | 522/34 |
| 4,861,916 A | 8/1989 | Köhler et al. ............... | 568/337 |
| 4,871,646 A | 10/1989 | Hayase et al. ............... | 430/192 |
| 4,929,647 A | 5/1990 | Burger et al. ................. | 522/99 |
| 5,017,406 A | 5/1991 | Lutz ......................... | 427/54.1 |
| 5,420,222 A | 5/1995 | Stepp et al. .................. | 528/31 |
| 5,532,112 A | 7/1996 | Kohler et al. ............ | 430/281.1 |
| 5,612,389 A | 3/1997 | Chabrecek et al. .......... | 522/35 |
| 5,744,512 A | 4/1998 | Kohler et al. ................. | 522/34 |
| 5,776,658 A | 7/1998 | Niesert et al. .......... | 430/281.1 |
| 5,837,746 A | 11/1998 | Kohler et al. .................. | 522/8 |
| 6,197,842 B1 | 3/2001 | Marchin et al. ............... | 522/35 |
| 2001/0007880 A1 | 7/2001 | Marchin et al. ............... | 522/35 |

FOREIGN PATENT DOCUMENTS

| | | |
|---|---|---|
| EP | 0088842 | 9/1983 |
| EP | 0161830 | 11/1985 |
| EP | 0162572 | 11/1985 |
| WO | 97/49768 | 12/1997 |
| WO | 98/00456 | 1/1998 |

OTHER PUBLICATIONS

A. Kolar et al., Pure Appl. Chem., A31(3), (1994), pp. 305–318.

*Primary Examiner*—Susan W. Berman
(74) *Attorney, Agent, or Firm*—Tyler A. Stevenson

(57) ABSTRACT

The invention relates to the use of surface-active photoinitiators of formula I

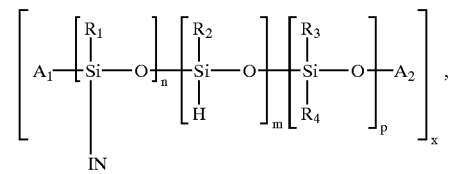

the units being arranged randomly or in blocks, and wherein n is a number from 1 to 1000; m is a number from 0 to 100; p is a number from 0 to 10,000; x is the number 1, or, when n is 1, x may also be the number 2; $A_1$ and $A_2$ are, for example, $C_1$–$C_{18}$alkyl; or $A_1$ and $A_2$ together are a single bond; $R_1$, $R_2$ and $R_3$ are, for example, each independently of the others $C_1$–$C_{18}$alkyl, phenyl or $C_5$–$C_8$cycloalkyl; $R_4$ is, for example, unsubstituted or substituted $C_1$–$C_{18}$alkyl, unsubstituted or substituted phenyl or $C_5$–$C_8$cycloalkyl; IN, when x is 1, is a radical of formula

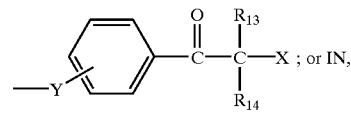

when x is 2, is a radical of formula

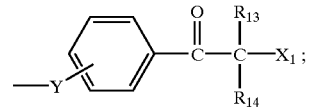

$R_{13}$ and $R_{14}$ are, for example, each independently of the other $C_1$–$C_{12}$alkyl; Y is, for example, —$(CH_2)_a$—O—; X is $OR_{15}$ or $N(R_{16})(R_{17})$; $R_{15}$ is, for example, hydrogen or $C_1$–$C_4$alkyl; $R_{16}$ and $R_{17}$ are, for example, hydrogen or $C_1$–$C_{12}$alkyl; $X_1$ has, for example, one of the meanings of X; and $R_{18}$ is, for example, —$(CH_2)_a$—;
in photochemically and combined photochemically and thermally crosslinkable formulations.

5 Claims, No Drawings

SURFACE-ACTIVE PHOTOINITIATORS

This is a divisional of application Ser. No. 09/618,821, filed on July 18, 2000. now U.S. Pat. No. 6,376,568.

The invention relates to a process for the preparation of scratch-resistant durable coatings in which siloxane-containing photoinitiators are used as surface-active initiators, and to new surface-active photoinitiators.

In order to improve the miscibility of photoinitiators with silicone-containing substrates (compatibility) that are to be photochemically crosslinked, WO 97/49768, U.S. Pat. No. 5,776,658, U.S. Pat No. 4,391,963 and EP 88842, for example, propose photoinitiators, e.g. of the hydroxyketone, aminoketone, benzoin ether, benzophenone or thioxanthone type, that have been modified with silyl radicals, especially with polymeric silyl radicals. Patent Specifications U.S. Pat No. 4,536,265, U.S. Pat No. 4,534,838 and EP 162572 also describe a wide variety of photoinitiator structures provided with organopolysiloxane radicals. Those compounds are derived, for example, from dialkoxyacetophenones and have enhanced solubility in silicone substrates. U.S. Pat No. 4,507,187 discloses silyl-group-containing diketo photoinitiators as photoinitiators that are readily soluble in silicone polymers, and also the polymers obtained with those initiators. U.S. Pat. No. 4,477,326 describes self-polymerising siloxane polymers that contain photoinitiator units as groups that trigger the polymerisation reaction. Polymeric photoinitiators containing siloxane radicals are described in U.S. Pat. No. 4,587,276.

In J.M.S. Pure Appl. Chem. A31(3) (1994), 305–318, A. Kolar, H. F. Gruber and G. Greber describe reactive silyl-derived α-hydroxyketone photoinitiators. The literature references mentioned are concerned especially with solving the problem of improving the miscibility of the photoinitiators with the substrate to be polymerised, that is to say distributing the initiator in the substrate as homogeneously as possible. WO 98/00456 proposes certain coating compositions, and a curing process by means of which the properties of the coating surface can be improved.

New energy-saving curing mechanisms and applications that result in as few emissions as possible are sought by the coatings industry in order to produce durable, scratch-resistant coatings. There is especially a need to improve the surface of coatings, especially in respect of hardness, durability and gloss properties.

It has now been found that the desired properties can be obtained using certain photoinitiators in the coatings that are to be cured. For that purpose, the photoinitiator is not distributed as homogeneously as possible in the formulation to be cured but is concentrated in targeted manner at the surface of the coating to be cured; the initiator is thus oriented in targeted manner towards the surface of the formulation. For that purpose it is necessary to use photoinitiators that have been designed in a particular manner.

The invention relates to a process for the preparation of coatings having scratch-resistant durable surfaces, in which
(I) a photocurable formulation comprising
  (A) an ethylenically unsaturated polymerisable compound; and
  (B) a photoinitiator;
is prepared;
(II) that formulation is applied to a support; and
(III) the formulation is cured either solely by irradiation with electromagnetic radiation of a wavelength of from 200 to 600 nm, or by irradiation with electromagnetic radiation of a wavelength of from 200 to 600 nm and by prior, simultaneous and/or subsequent action of heat;

in which process the formulation comprises as photoinitiator (B) at least one surface-active photoinitiator that is concentrated at the surface of the formulation.

A surface-active photoinitiator is used as photoinitiator (B). Photoinitiator (B) is a photoinitiator compound that is incompatible with the formulation to be cured, that is to say has poor miscibility therewith, and is therefore able to concentrate at the surface of the formulation.

A suitable surface-active photoinitiator (B) in the process described above is a compound comprising
a customary photocleavable photoinitiator molecule moiety (b1) and
a molecule moiety (b2) that is incompatible with the formulation to be cured.

Customary photocleavable molecule moieties are known to the person skilled in the art, and are, for example, α-cleaving radicals. Of special interest are compounds in which the photocleavable photoinitiator molecule moiety (b1) contains a group

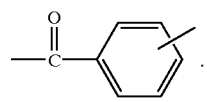

The molecule moiety (b2) having poor compatibility with the formulation to be cured is a siloxane radical.

Suitable photoinitiators (B) are especially compounds of formula I

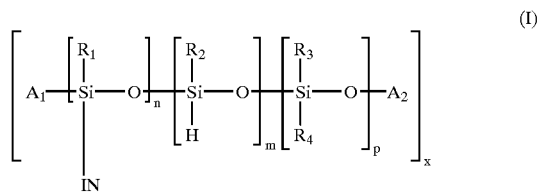

wherein the units of formulae Ia, Ib and/or Ic

are arranged randomly or in blocks, and wherein n is a number from 1 to 1000, or, when the siloxane starting material is a mixture of oligomeric siloxanes, n may also be less than 1, but greater than 0;

m is a number from 0 to 100;

p is a number from 0 to 10 000;

x is the number 1 or 2;

$A_1$ is $C_1$–$C_{18}$alkyl or a radical of formula $$-O-\underset{R_7}{\overset{R_5}{\underset{|}{\overset{|}{Si}}}}-R_6;$$

$A_2$ is $C_1$–$C_{18}$alkyl or a radical of formula $$-\underset{R_{10}}{\overset{R_8}{\underset{|}{\overset{|}{Si}}}}-R_9;$$

or $A_1$ and $A_2$ together are a single bond;

$R_1$, $R_2$, $R_3$, $R_5$, $R_6$, $R_7$, $R_8$, $R_9$ and $R_{10}$ are each independently of the others $C_1$–$C_{18}$alkyl, phenyl, $C_2$–$C_6$hydroxyalkyl, $C_2$–$C_6$aminoalkyl or $C_5$–$C_8$cycloalkyl;

$R_4$ is $C_1$–$C_{18}$alkyl; $C_1$–$C_{18}$alkyl substituted by hydroxy, $C_1$–$C_{12}$alkoxy, halogen, $C_3$–$C_8$-cycloalkyl and/or by $N(R_{11})(R_{12})$; or $R_4$ is phenyl; phenyl substituted by $C_1$–$C_{12}$alkyl, $C_1$–$C_{12}$-alkoxy, halogen, hydroxy and/or by $N(R_{11})(R_{12})$; or $R_4$ is $C_5$–$C_8$cycloalkyl;

$R_{11}$ and $R_{12}$ are each independently of the other hydrogen, $C_1$–$C_{12}$alkyl or $C_1$–$C_{12}$hydroxyalkyl, or $R_{11}$ and $R_{12}$ together are $C_2$–$C_8$alkylene, which may be interrupted by an oxygen atom;

IN when x is 1, is a radical of formula

IN when x is 2, is a radical of formula $R_{13}$ and $R_{14}$ are each independently of the other $C_1$–$C_{12}$alkyl, $C_2$–$C_8$alkenyl, $C_5$–$C_8$cycloalkyl, phenyl-$C_1$–$C_3$alkyl; or $R_{13}$ and $R_{14}$ together are $C_2$–$C_8$alkylene, $C_3$–$C_9$oxaalkylene or $C_3$–$C_9$-azaalkylene;

Y is —$(CH_2)_a$—, —$(CH_2)_a$—O—, —O—$(CH_2)_a$—O—, —$(CH_2)_b$—O—$(CH_2)_a$—, —$(CH_2)_b$—O—$(CH_2)_a$—O—, —$(CH_2)_a$—N($R_{12}$)— —$(CH_2)_b$—O—$(CH_2)_a$—N($R_{12}$)—, —($C_2$–$C_{10}$alkenylene)—O—, —($C_2$–$C_{10}$alkenylene)—N($R_{12}$)—, —($C_2$–$C_{10}$alkenylene)—O—$(CH_2)_a$—O— or —($C_2$–$C_{10}$alkenylene)—O—$(CH_2)_a$—N($R_{12}$)—;

a and b are each independently of the other a number from 0 to 10;

X is $OR_{15}$ or $N(R_{16})(R_{17})$;

$R_{15}$ is hydrogen, $C_1$–$C_4$alkyl, $C_2$–$C_8$alkenyl or $C_1$–$C_4$alkanoyl;

$R_{16}$ and $R_{17}$ are each independently of the other hydrogen, $C_1$–$C_{12}$alkyl or $C_2$–$C_6$alkenyl; or $R_{16}$ and $R_{17}$ together are $C_4$–$C_5$alkylene and, together with the nitrogen atom to which they are bonded, form a 5- or 6-membered ring, which may be interrupted by O or by $N(R_{12})$; and $X_1$ is a radical —O—, —O—$(CH_2)_a$— or —N($R_{12}$)—$(CH_2)_a$—.

A number of compounds of formula I are novel and form part of the subject matter of the present Application.

$C_1$–$C_{18}$Alkyl is linear or branched and is, for example, $C_1$–$C_{12}$-, $C_1$–$C_8$-, $C_1$–$C_6$- or $C_1$–$C_4$-alkyl. Examples thereof are methyl, ethyl, propyl, isopropyl, n-butyl, sec-butyl, isobutyl, tert-butyl, pentyl, hexyl, heptyl, 2,4,4-trimethylpentyl, 2-ethylhexyl, octyl, nonyl, decyl, undecyl, dodecyl, hexadecyl and octadecyl. For example, $R_1$, $R_2$, $R_3$, $R_4$, $R_5$, $R_6$, $R_7$, $R_8$, $R_9$ and $R_{10}$ are $C_1$–$C_8$alkyl, especially $C_1$–$C_6$alkyl, preferably $C_1$–$C_4$alkyl, such as methyl or butyl, especially methyl.

$C_1$–$C_{12}$Alkyl, $C_1$–$C_{10}$alkyl and $C_1$–$C_8$alkyl are also linear or branched and have, for example, the meanings given above up to the corresponding number of carbon atoms.

Substituted alkyl is, for example, mono- to penta-substituted, mono- to tri-substituted or mono- or di-substituted.

Alkyl substituted by halogen is substituted, for example, by fluorine, chlorine, bromine or iodine.

Alkyl substituted by OH is mono- or poly-substituted, especially mono-substituted, by OH. Examples thereof are 2-hydroxyeth-1-yl, 3-hydroxyprop-1-yl and hydroxymethyl.

$C_2$–$C_6$Hydroxyalkyl is hydroxy-substituted $C_2$–$C_6$alkyl, wherein the alkyl has the meanings given above according to the number of carbon atoms.

$C_2$–$C_6$Aminoalkyl is $C_2$–$C_6$alkyl substituted by an amino radical, especially by —$NH_2$, wherein the alkyl has the meanings given above according to the number of carbon atoms.

$C_2$–$C_8$Alkylene is linear or branched, such as ethylene, propylene, isopropylene, n-butylene, sec-butylene, isobutylene, tert-butylene, pentylene, hexylene, heptylene or octylene. When $R_{13}$ and $R_{14}$ together are $C_2$–$C_8$alkylene, they are especially pentylene, that is to say, together with the carbon atom to which they are bonded, they form a cyclohexyl ring, the following structure being intended especially $C_3$–$C_9$Oxaalkylene and $C_3$–$C_9$azaalkylene are alkylene, as described above, interrupted by O— or by $N(R_{12})$.

$C_5$–$C_8$Cycloalkyl is linear or branched alkyl containing at least one ring, for example cyclopentyl, methylcyclopentyl, cyclohexyl, methyl- or dimethyl-cyclohexyl or cyclooctyl, especially cyclopentyl and cyclohexyl.

$C_1$–$C_{12}$Alkoxy denotes linear or branched radicals and is, for example, $C_1$–$C_8$-, $C_1$–$C_6$- or $C_1$–$C_4$-alkoxy. Examples thereof are methoxy, ethoxy, propoxy, isopropoxy, n-butyloxy, sec-butyloxy, isobutyloxy, tert-butyloxy, pentyloxy, hexyloxy, heptyloxy, 2,4,4-trimethylpentyloxy, 2-ethylhexyloxy, octyloxy, nonyloxy, decyloxy and dodecyloxy, especially methoxy, ethoxy, propoxy, isopropoxy, n-butyloxy, sec-butyloxy, isobutyloxy, tert-butyloxy, preferably methoxy. $C_1$–$C_8$Alkoxy is also linear or branched and has, for example, the meanings given above up to the corresponding number of carbon atoms.

$C_2-C_8$Alkenyl is mono- or poly-unsaturated and linear or branched, and is, for example, $C_2-C_6$- or $C_2-C_4$-alkenyl. Examples thereof are allyl, methallyl, 1,1-dimethylallyl, 1-butenyl, 2-butenyl, 1,3-pentadienyl, 1-hexenyl and 1-octenyl, especially allyl. $R_{13}$ and $R_{14}$ as $C_2-C_8$alkenyl are, for example, $C_2-C_6$alkenyl, especially $C_2-C_4$alkenyl.

$C_2-C_{10}$Alkenylene is a divalent radical that is mono- or poly-unsaturated and linear or branched, and is, for example, $C_2-C_6$- or $C_2-C_4$-alkenylene. Examples thereof are allylene, methallylene, 1,1-dimethylallylene, vinylene, 1-butenylene, 2-butenylene, 1,3-pentadienylene, 1-hexenylene and 1-octenylene, especially allylene.

$C_1-C_4$Alkanoyl is linear or branched and is, for example, formyl, acetyl, propionyl, butanoyl or isobutanoyl.

Halogen is fluorine, chlorine, bromine or iodine, for example fluorine, chlorine or bromine, especially chlorine or fluorine.

Phenyl-$C_1-C_3$alkyl is, for example, benzyl, phenylethyl, α-methylbenzyl or α,α-dimethylbenzyl, especially benzyl.

When $R_{16}$ and $R_{17}$ together with the nitrogen atom to which they are bonded form a 6-membered aliphatic ring, which may be interrupted by a further nitrogen or oxygen atom, it is, for example, a morpholinyl, piperidinyl or piperazinyl ring.

When $R_{11}$ and $R_{12}$ together are $C_2-C_8$alkylene that may be interrupted by an oxygen atom, they form together with the nitrogen atom to which they are bonded, for example, a piperidinyl or morpholinyl ring.

The units of formulae Ia, Ib and/or Ic are arranged randomly or in blocks, that is to say in the formula drawing given for formula I the units may be arranged in any order. For example, blocks of units of formulae Ia, Ib and Ic may follow one another, but the individual units may also be linked in random distribution, depending upon the siloxane used during preparation. The expression "and/or" indicates that not just one of the defined alternatives (e.g. substituents) may be present, but that it is also possible for a plurality of different defined alternatives (e.g. substituents) to be present together, that is to say mixtures of different alternatives (e.g. substituents) may be present.

The expression "at least one" is intended to mean one or more than one, for example one or two or three, preferably one or two.

$R_{13}$ and $R_{14}$ are, for example, $C_1-C_4$alkyl, especially methyl. Preferably $R_{13}$ and $R_{14}$ are methyl or together are $C_3-C_8$alkylene; in particular, together with the carbon atom to which they are bonded they form a cyclohexylring, or $R_{13}$ is $C_1-C_4$alkyl, especially ethyl, and $R_{14}$ is allyl or benzyl.

"a" is preferably a number from 0 to 10, e.g. from 0 to 3, especially 3; "n" is preferably from 1 to 100; "p" is, for example, from 1 to 1000, from 1 to 100, from 1 to 50 or from 1 to 25; and "m" is from 0 to 100, e.g. from 0 to 50 or from 0 to 25, especially 0.

When the siloxane starting material is a mixture of oligomeric siloxanes, "n" may also be less than 1, but greater than 0. In that case, "n" is, for example, a number from 0.1 to 1000, from 0.5 to 1000, from 0.8 to 1000, etc.

X is preferably $OR_{15}$ and $R_{15}$ is preferably hydrogen.

Y is preferably $-(CH_2)_a-O-$, $-(CH_2)_a-O-(CH_2)_a-$ or $-(CH_2)_a-O-(CH_2)_a-O-$, where a is especially 3.

In the IN group, Y is especially positioned on the phenyl ring in the para-position relative to the carbonyl group.

$R_{16}$ and $R_{17}$ are especially $C_1-C_4$alkyl, preferably methyl, or together with the nitrogen atom to which they are bonded form a morpholinyl radical.

$R_1$, $R_2$ and $R_3$ are preferably $C_1-C_4$alkyl, especially methyl.

$R_4$ is especially $C_1-C_4$alkyl, for example methyl.

Preference is given to a process as described above in which the surface-active photoinitiator (B) is a compound of formula I, wherein n is a number from 1 to 10, or, when the siloxane starting material is a mixture of oligomeric siloxanes, n may also be less than 1, but greater than 0;

m is a number from 0 to 25;

p is a number from 0 to 25;

$A_1$ is $C_1-C_4$alkyl or a radical of formula

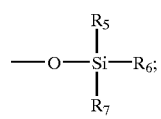

$A_2$ is $C_1-C_4$alkyl or a radical of formula

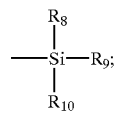

or $A_1$ and $A_2$ together are a single bond;

$R_1$, $R_2$, $R_3$, $R_5$, $R_6$, $R_7$, $R_8$, $R_9$ and $R_{10}$ are each independently of the others $C_1-C_4$alkyl;

$R_4$ is $C_1-C_4$alkyl;

$R_{13}$ and $R_{14}$ are each independently of the other $C_1-C_4$alkyl; or $R_{13}$ and $R_{14}$ together are $C_2-C_8$alkylene;

Y is $-(CH_2)_a-O-$, $-(CH_2)_b-O-(CH_2)_a-$ or $-(CH_2)_b-O-(CH_2)_a-O-$;

a and b are each independently of the other the number 2 or 3;

$R_{15}$ is hydrogen;

$R_{16}$ and $R_{17}$ together are $C_4-C_5$alkylene and together with the nitrogen atom to which they are bonded form a 6-membered ring interrupted by O; and $X_1$ is a radical $-O-(CH_2)_a-$.

Of special interest are the compounds

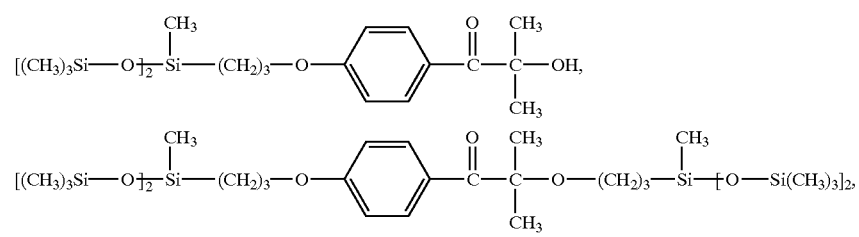

-continued
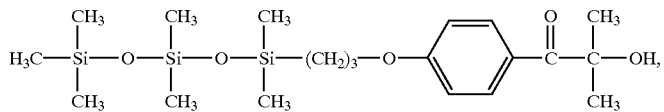
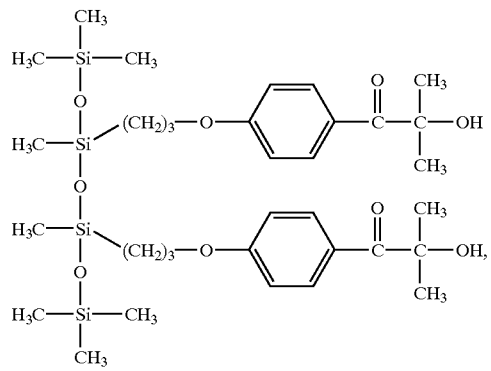
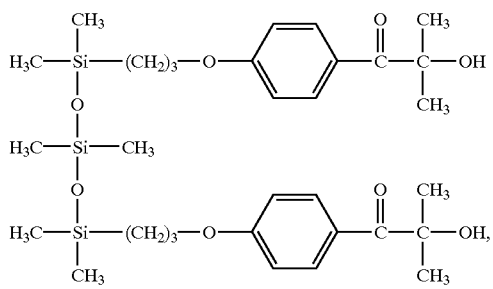
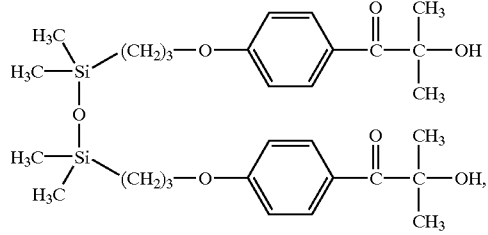
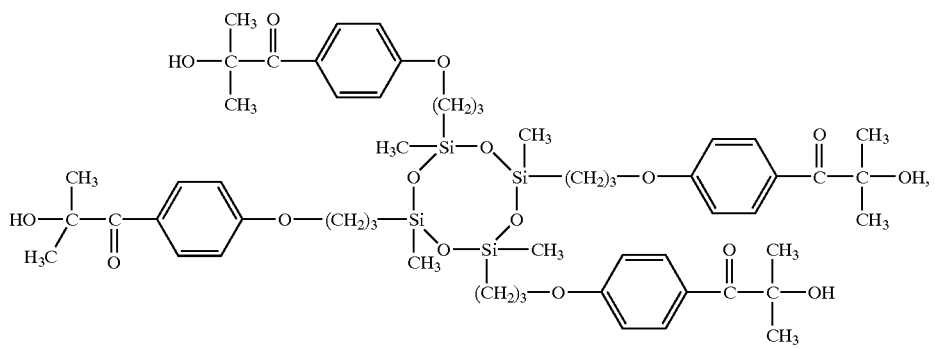
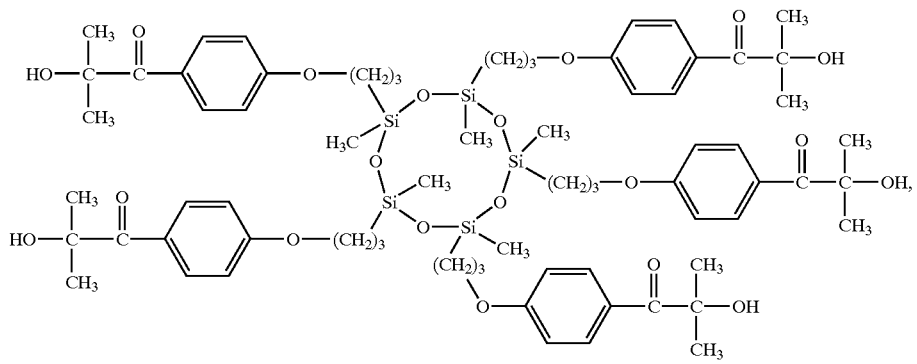
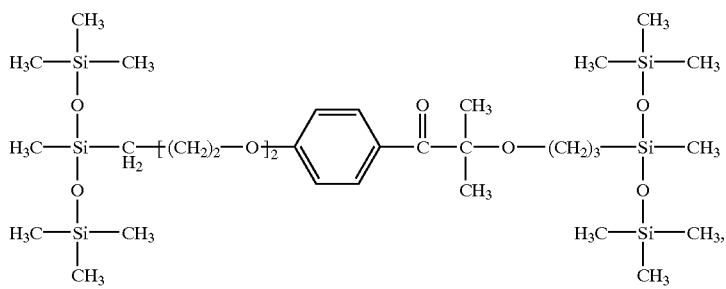

-continued
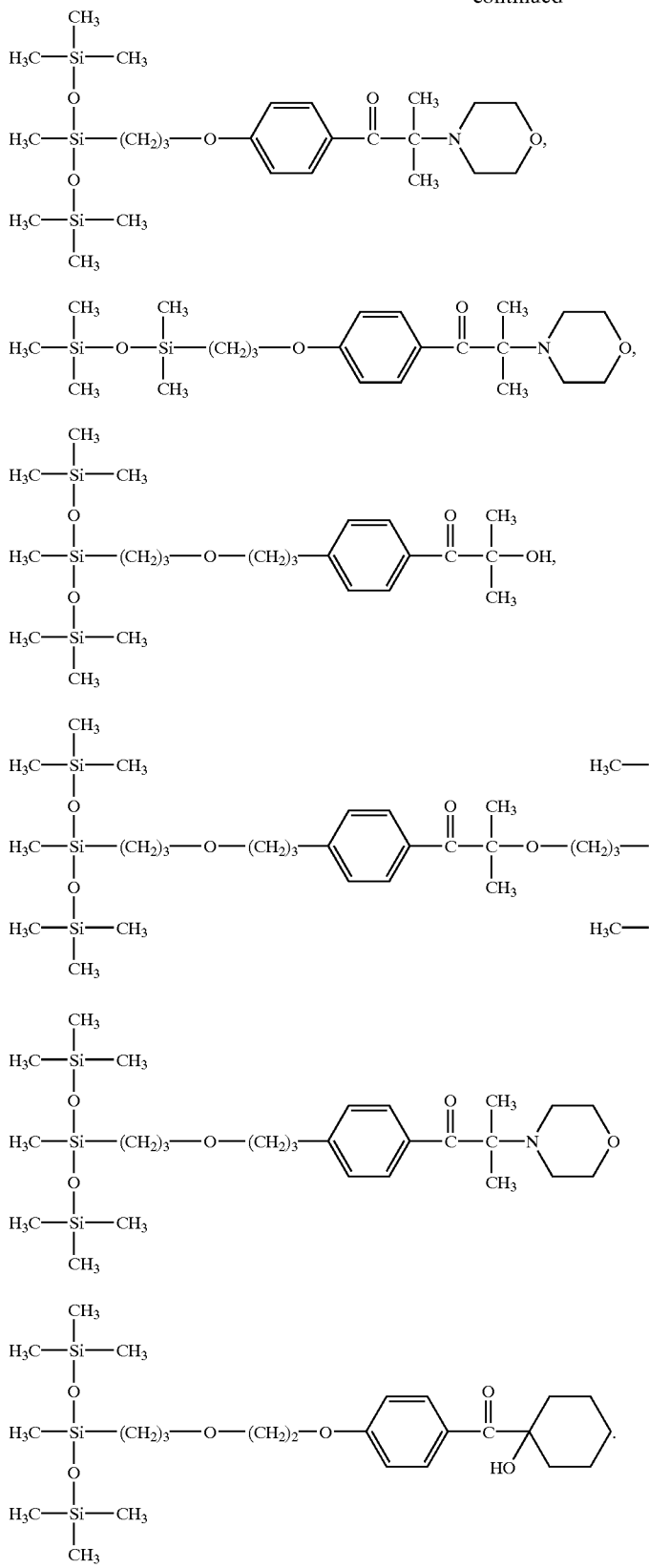
The compound of formula I are prepared according to customary methods known to the person skilled in the art.
Thus, compounds of formula I may be obtained, foe example, by reacting a photoinitiator with at least one alkenyl radical (IV) or (IVa) and a siloxane (V) in the presence of a suitable catalyst:

and the desired degree of substitution of those groups in the particular case. If all the groups are to react, it is

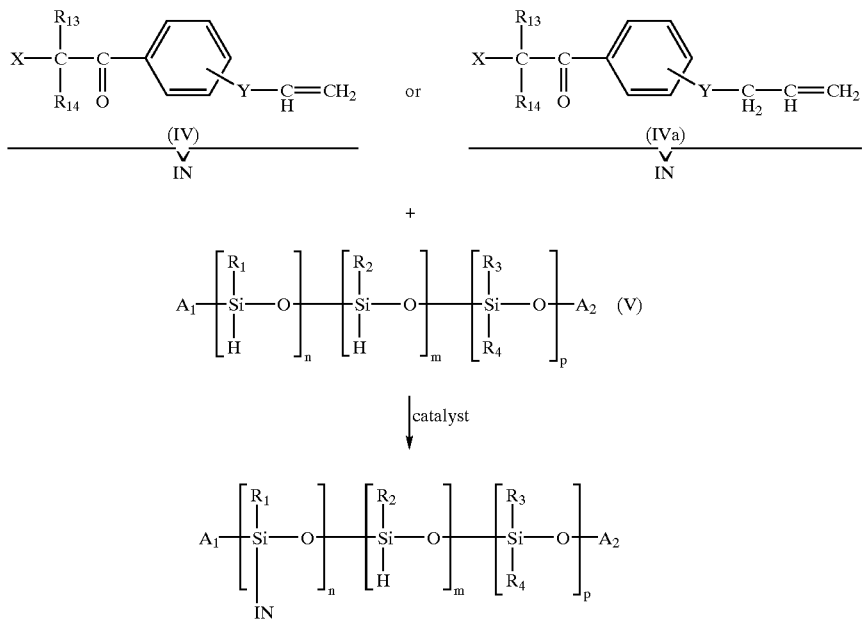

wherein IN, $R_1$, $R_2$, $R_3$, $R_4$, $R_{13}$, $R_{14}$, X, Y, $A_1$, $A_2$, n, m and p are as defined above.

In order to prepare compounds of formula I wherein x=2, suitably modified photoinitiators are used, that is to say those having, for example, 2 alkylene units.

The alkylene unit may, for example, be present at a different position on the photoinitiator molecule and the linkage to the siloxane is then effected in that position:

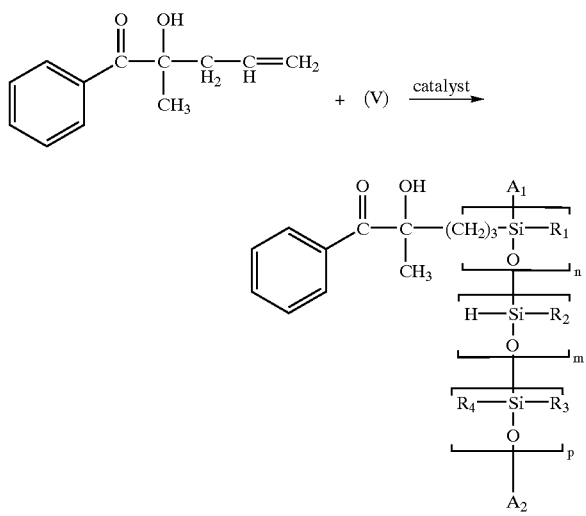

Such reactions are described, for example, in U.S. Pat. No. 4,391,963, EP 162572 or N. S. Allen et al., J. Photochem. Photobiol. A: Chem. 62 (1991), 125–139.

Reaction conditions for such reactions will be known to the person skilled in the art. The molar ratios of the alkenyl-modified compound (IV) and the siloxane compound (V) are dependent upon the desired product and are generally not critical. For example, the amount of (IV) to be used will be selected according to the content of free Si—H groups in (V)

advantageous, for example, to use (IV) in excess. It is also possible, however, to use an excess of component (V).

The reaction temperatures are advantageously kept within a range of from 20 to 150° C., preferably from 60 to 110° C. It is also advantageous to carry out the reaction, for example, in a suitable aprotic organic solvent, such as tetrahydrofuran (THF), dioxane, hexane, heptane, cyclohexane, toluene, xylene, benzene or chlorobenzene. The reaction may, however, also be carried out, for example, without solvent.

The reaction mixture will usually be stirred while the reaction is being carried out.

It is also advantageous to carry out the reaction under inert conditions, for example under an argon or nitrogen atmosphere.

Catalysts suitable for carrying out the reaction are, for example, noble metal catalysts, such as platinum or rhodium catalysts. Examples thereof are $H_2PtCl_6$ and $PtCl_2(C_6H_5—CH=CH_2)_2$. Such catalysts may, for example, also be applied to suitable support materials, for example aluminium oxide, such as $Pt/Al_2O_3$ (for example, obtainable from Heraeus). Examples of suitable catalysts are platinum, palladium, rhodium, nickel, cobalt, or other metals in powdered form or in complexes; platinum sponge, platinum black, chloroplatinic acid, the reaction product of chloroplatinic acid and alcohol, a complex of chloroplatinic acid and vinyl siloxane. Such catalysts are commercially available, for example platinum/-carbonyl/cyclovinylmethylsiloxane complex, platinum/divinyltetramethyldisiloxane complex, platinum/octanealdehyde/octanol complex, or may be obtained according to methods customary in the art and known to the person skilled in the art.

The concentration of the catalyst is advantageously, for example, from 1 to 1000 ppm, for example from 150 to 400 ppm.

A further possible method of preparing the surface-active photoinitiators is to react a photoinitiator that contains a suitable silyl group with an alkenyl-modified siloxane:

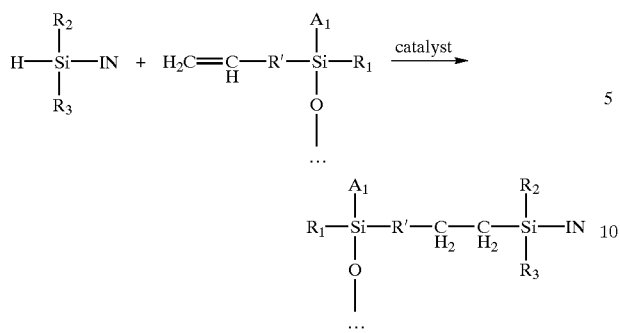

$R_1$, $R_2$, $R_3$, IN and $A_1$ are as defined above; R' is an alkylene radical;

". . ." indicates that the radical of the siloxane molecule moiety defined in formula I is attached at that position (according to formula I in this reaction in the starting material m must be 0). The reaction conditions for this method correspond to those described above. Such reactions are described in the literature, for example, in U.S. Pat. No. 4,391,963 and in JMS Pure Applied Chem. A31(3) (1994), 305.

The surface-active photoinitiators may, for example, also be obtained by reacting an OH— group-containing initiator with a siloxane:

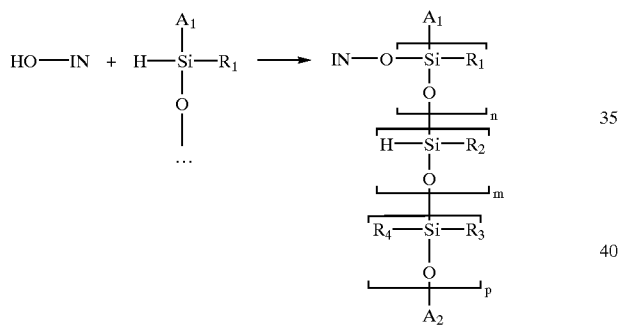

$R_1$, $R_2$, $R_3$, IN, $A_1$, n, m, p, $R_4$ and $A_2$ are as defined above; ". . ." indicates that the radical of the siloxane molecule moiety defined in formula I is attached at that position.

Suitable catalysts for this reaction are, for example, tin octoate, dibutyltin dilaurate, zinc octanoate, tin octanoate and zinc octanoate. Examples of such reactions (although the examples contain a sensitiser unit instead of a photoinitiator unit) can be found in U.S. Pat. No. 4,921,589.

In JMS Pure Appl. Chem. A 34(11) (1997), 2335–2353, L. Lecamp et al. describe a method for preparing siloxane-containing initiators in which an initiator containing an Si(OR)$_{1-3}$ group and a siloxane having an Si—(OH)$_{1-2}$ group are reacted. The catalyst used is, for example, di-butyltin dilaurate:

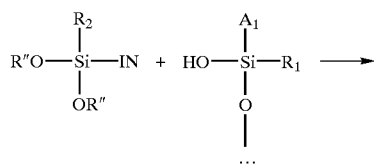

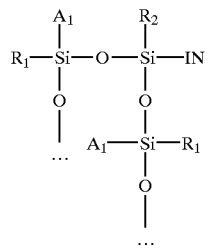

IN, $R_1$, $R_2$ and $A_1$ are as defined above; R" is alkyl, especially methyl; ". . ." indicates that the radical of the siloxane molecule moiety defined in formula I is attached at that position.

Surface-active photoinitiators according to the present invention can also be obtained, for example, by reacting a photoinitiator containing at least one carbonyl group on the aromatic ring with a siloxane containing a C—C double bond as terminal group (e.g. allyl or vinyl).

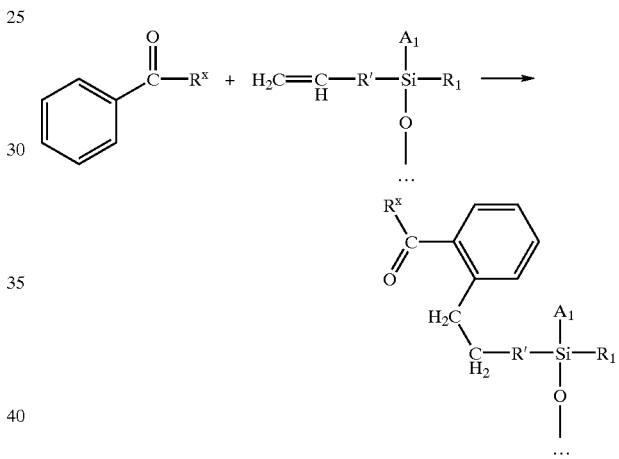

$R_1$ and $A_1$ are as defined above; $R^x$ together with the adjacent carbonyl group forms a benzoin, an α-hydroxyketone or an α-aminoketone; R' is alkylene; ". . ." indicates that the radical of the siloxane molecule moiety defined in formula I is attached at that position.

That reaction is published in U.S. Pat. No. 5,776,658. Suitable catalysts for that reaction are, for example, ruthenium compounds, as described by Murai et al. in Nature 366 (1993) 529.

U.S. Pat. No. 4,477,326 and JP 9-328522-A describe the polymerisation or copolymerisation of polyalkoxysiloxanes in the presence of a base or of an acid catalyst. The method described is suitable also for the preparation of surface-active initiators:

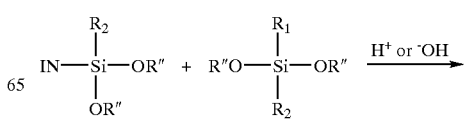

-continued

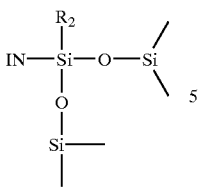

IN, $R_1$ and $R_2$ are as defined above; R" is alkyl.

In that reaction it is possible to obtain both polymeric and cyclic products.

A further possible method of preparing surface-active photoinitiators is described, for example, in U.S. Pat. Nos. 4,587,276 and 4,477,276, namely the polymerisation or copolymerisation of siloxanes having hydrolysable groups (e.g. Si—Cl) in the presence of water:

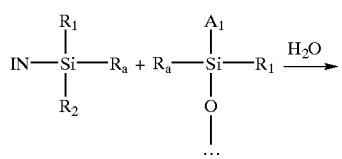

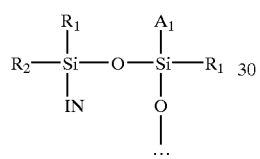

IN, $R_1$, $R_2$ and $A_1$ are as defined above; $R_a$ is, for example, Cl or $OCH_3$; "..." indicates that the radical of the siloxane molecule moiety defined in formula I is attached at that position.

In J.M.S. Pure Appl. Chem. A 31(3) (1994), 305–318, A. Kolar et al. describe the preparation of photoinitiators containing siloxane radicals starting from 1,4-dichlorobenzene. A Grignard reaction creates a reactive centre, which is reacted with dimethyldichlorosilane or dimethylmonochlorosilane to form the corresponding silyl-modified chlorobenzene, into which the appropriate α-cleavable photoinitiator carbonyl radical is introduced by further reactions.

In Makromol. Chem. 193 (1992) 1273–1282, L. Pouliquen et al. published a multi-step reaction of photoinitiators having acid groups and a siloxane having epoxy radicals in the presence of acetic anhydride (the photoinitiator compounds in that reference are of the phenone/tert-amine type)

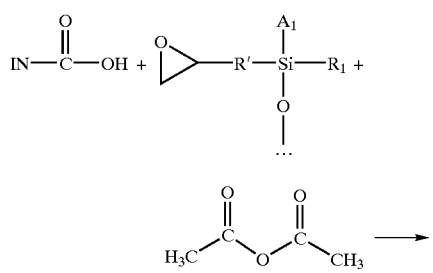

-continued

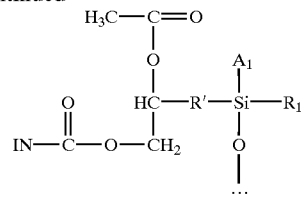

IN, $A_1$ and $R_1$ are as defined above; R' is alkylene; "..." indicates that the radical of the siloxane molecule moiety defined in formula I is attached at that position.

Isocyanate-group-containing photoinitiators and siloxanes having hydroxyl or amine groups may also be reacted to form surface-active photoinitiators:

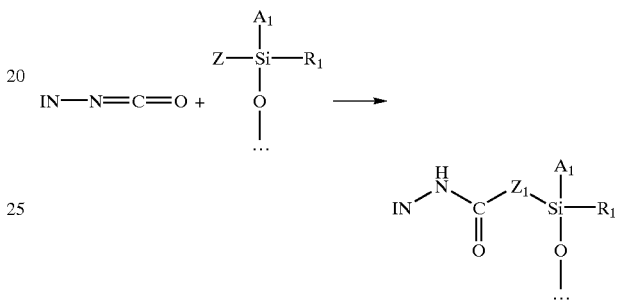

IN, $A_1$ and $R_1$ are as defined above; Z is $NH_2$ or OH; $Z_1$ is NH or O; "..." indicates that the radical of the siloxane molecule moiety defined in formula I is attached at that position. Such reactions are described, for example, in WO 96/20919.

Photoinitiators substituted by cyclic siloxane radicals may be obtained, for example, by carrying out the reactions described above with a cyclic siloxane, for example

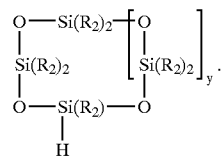

In order to prepare photoinitiators provided with cyclic siloxane radicals, it is also possible, however, firstly to introduce linear siloxane radicals, for example by means of the methods described above, and subsequently to cyclise them by the action of a base, for example sodium hydroxide, or by the action of an acid.

The synthesis of surface-active photoinitiators containing cyclic siloxane radicals can be carried out, for example, as described above by reacting a cyclic siloxane with the initiator moiety in question:

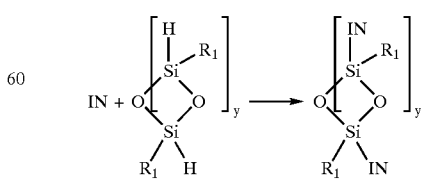

(IN and $R_1$ are as defined above; y determines the size of the ring) or by a cyclisation reaction of an OR-group-containing siloxane-modified initiator moiety in the presence of an acid or alkali:

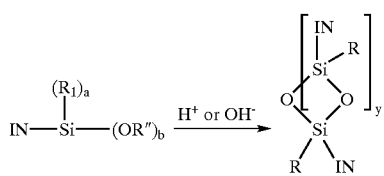
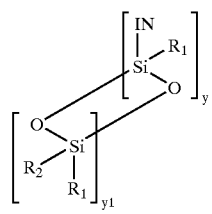

($R_1$ and IN are as defined above; R" is alkyl; a=0 or 1; b=1 or 2, where the sum of a+b=3; depending upon the value of a and b, R is either $R_1$ or OR")

Cyclic compounds can also be formed by reacting an OR-group-containing siloxane-modified initiator moiety with an OR-group-containing siloxane:

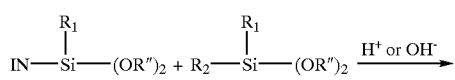

(IN, $R_1$ and $R_2$ are as defined above; R" is alkyl; the sum of y and y1 determines the number of ring members)

The distribution of the Si(IN)($R_1$) and Si($R_1$)($R_2$) groups will be either random or in blocks. The preparation of the surface-active photoinitiators may also yield mixtures of active compounds. Such mixtures can be separated by customary methods, such as distillation, crystallisation or chromatography, or they may be used as such as surface-active photoinitiators in compositions to be polymerised.

The invention relates also to photoinitiator mixtures comprising

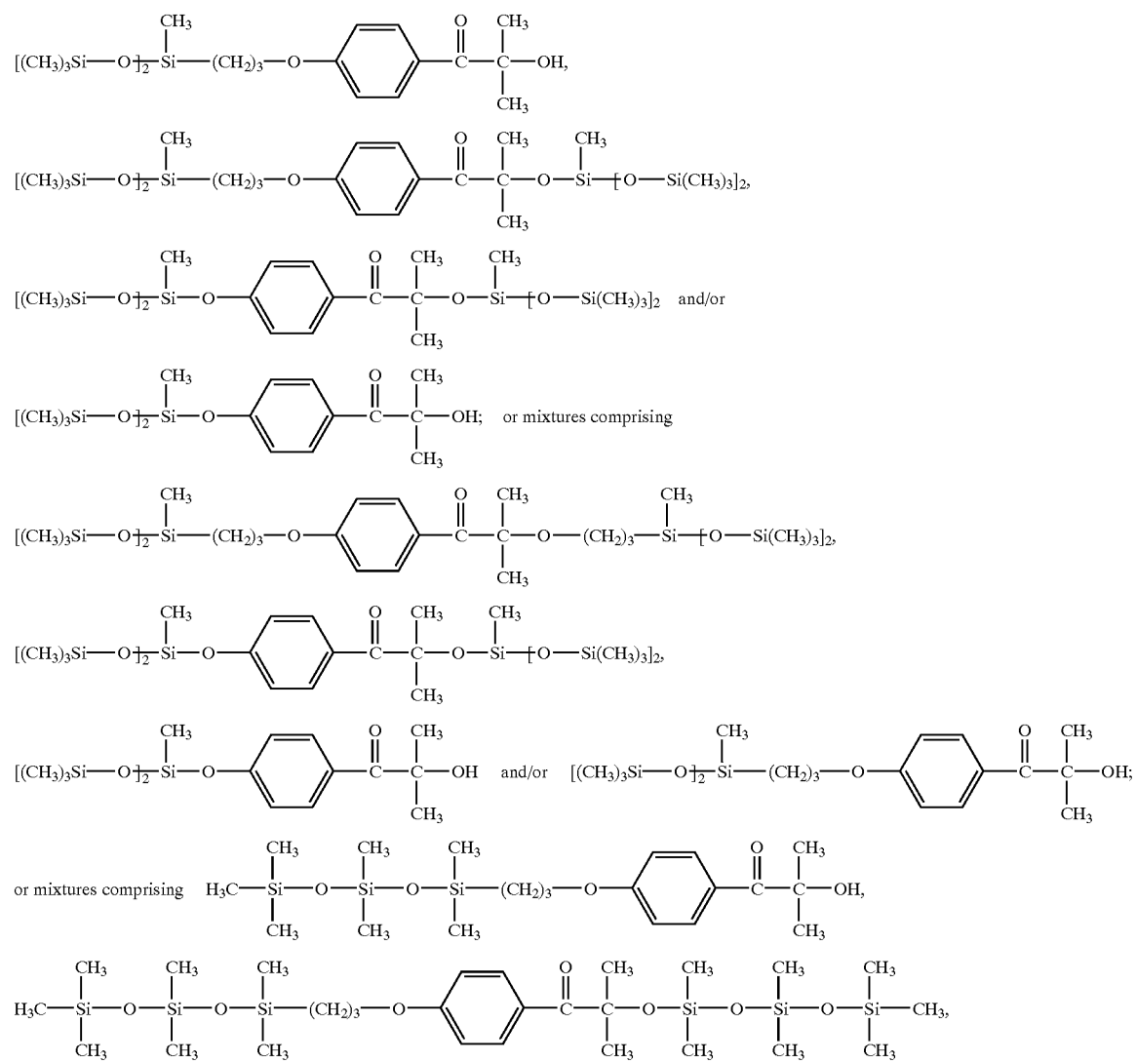

-continued

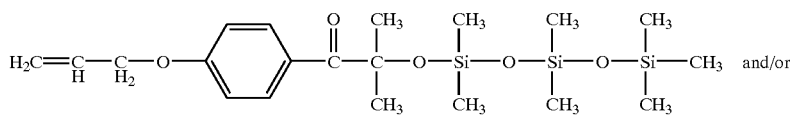 and/or

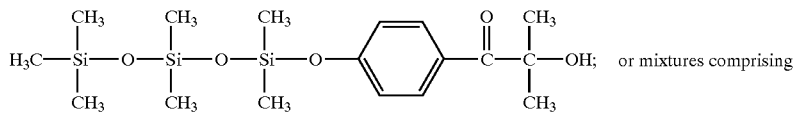 or mixtures comprising

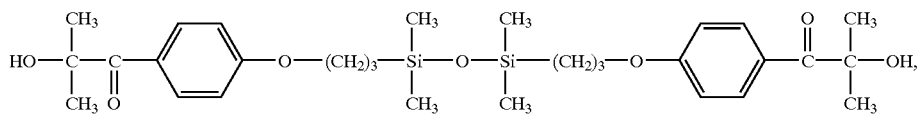

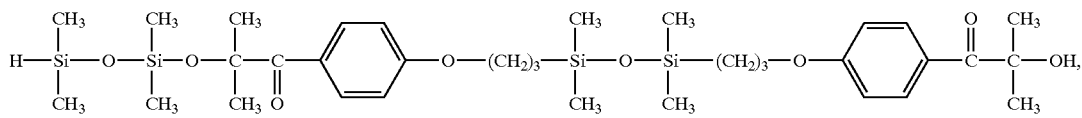

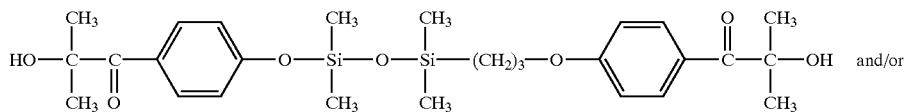 and/or

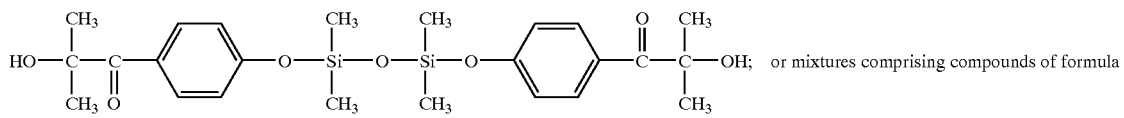 or mixtures comprising compounds of formula

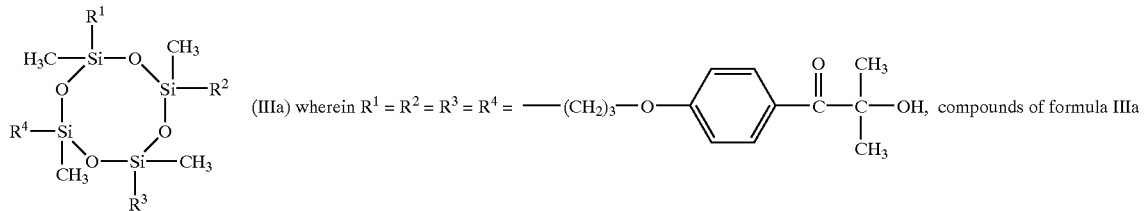 (IIIa) wherein $R^1 = R^2 = R^3 = R^4 =$ —(CH$_2$)$_3$—O—<phenyl>—C(=O)—C(CH$_3$)$_2$—OH, compounds of formula IIIa wherein $R^1 = R^2 = R^3 =$ —(CH$_2$)$_3$—O—<phenyl>—C(=O)—C(CH$_3$)$_2$—OH and $R^4 = $ H, and/or compounds of formula IIIa wherein $R^1 = R^2 = R^3 =$

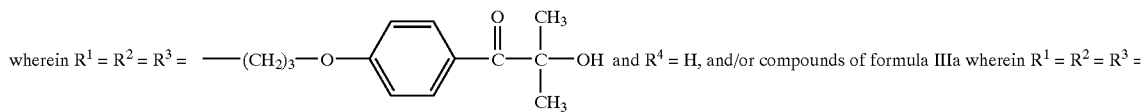 and $R^4 = $ —(CH$_2$)$_2$CH$_3$; or mixtures comprising compounds of formula

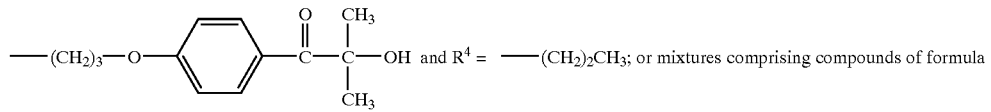 (IIIb) wherein $R^1 = R^2 = R^3 = R^4 = R^5 =$ —(CH$_2$)$_3$—O—<phenyl>—C(=O)—C(CH$_3$)$_2$—OH, compounds of formula IIIb wherein $R^1 = R^2 = R^3 = R^4 =$ 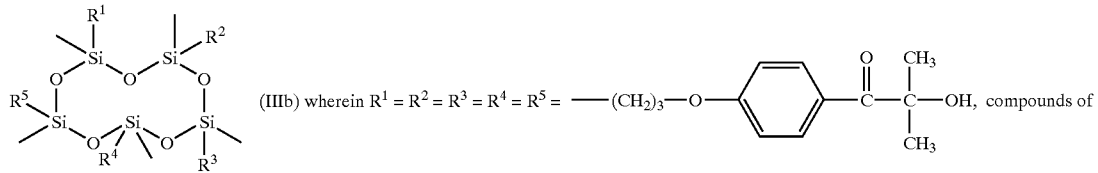 —OH and $R^5 = $ H and/or compounds of formula IIIb wherein $R^1 = R^2 = R^3 =$ 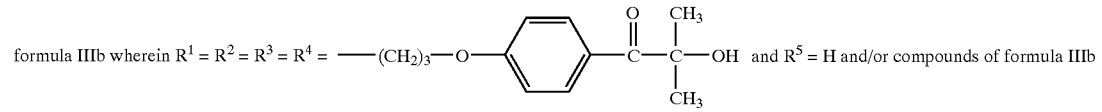 —OH and $R^4 = R^5 = $ H; or mixtures comprising

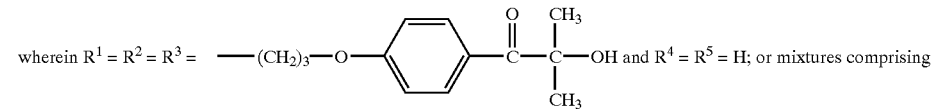

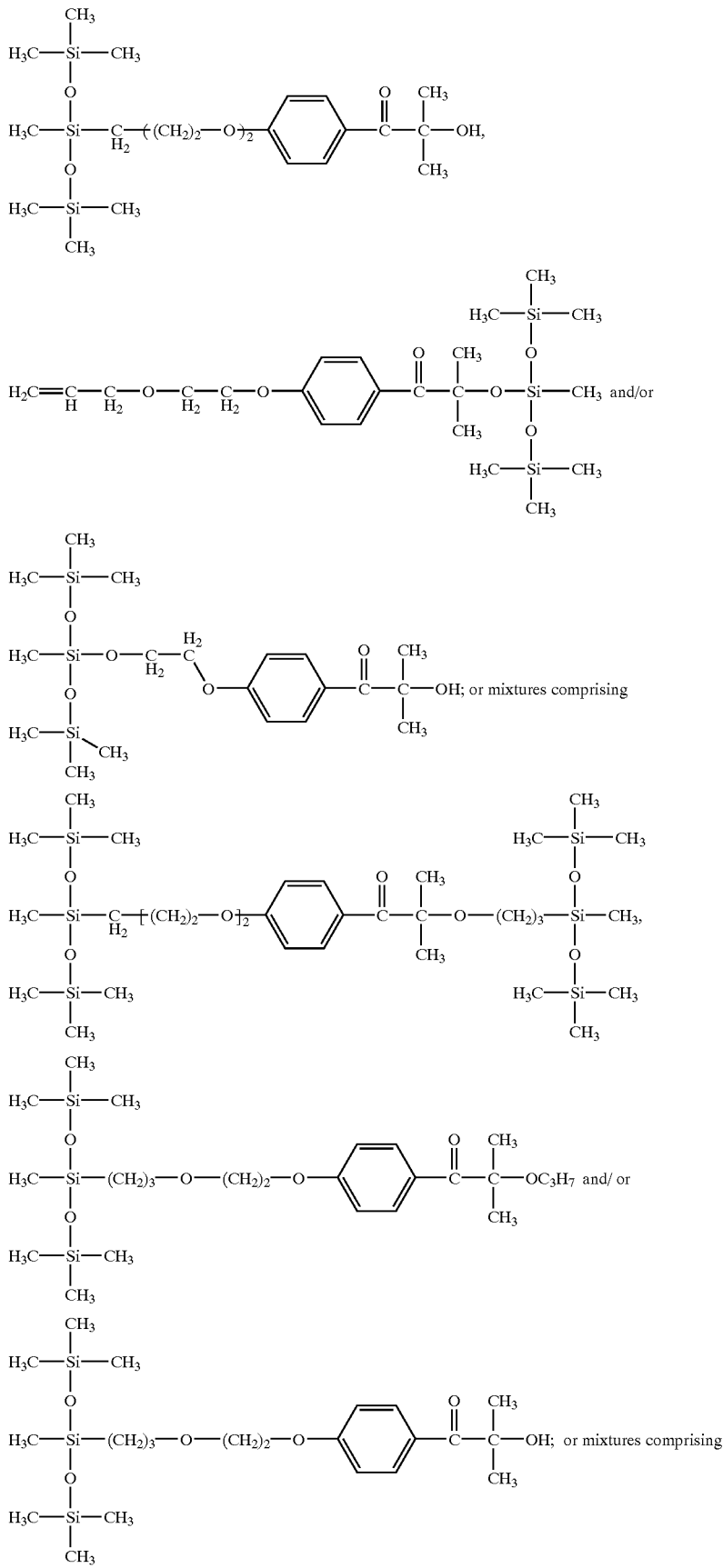

-continued
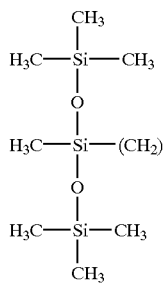
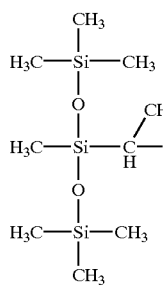
and/or 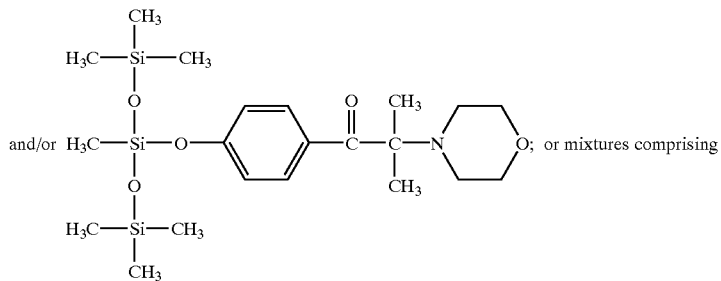 or mixtures comprising
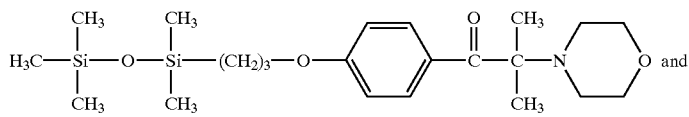 and
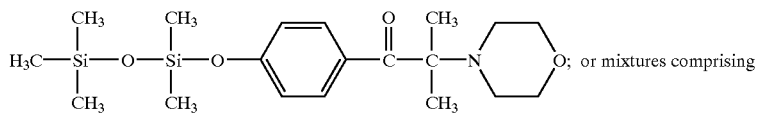 or mixtures comprising
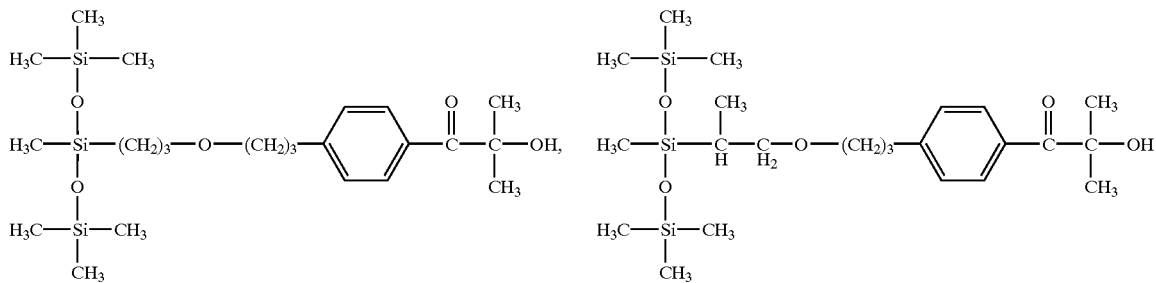
and/or 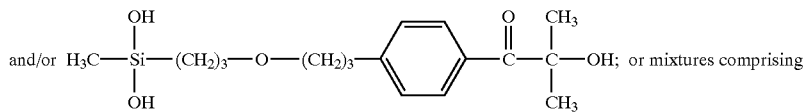 or mixtures comprising
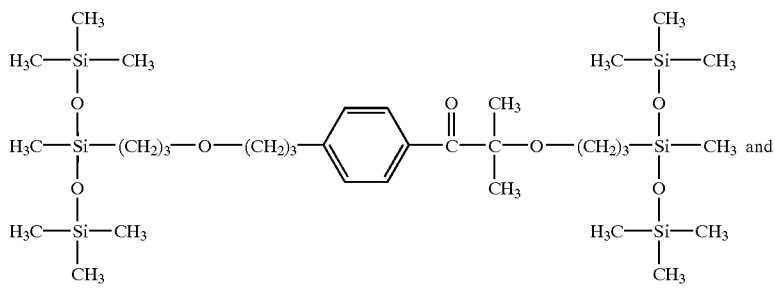

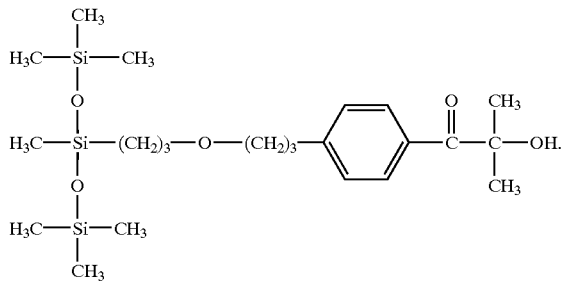

The alkenyl-modified photoinitiators (IV) can be prepared according to methods known to the person skilled in the art, for example according to the method described in EP 281941. Suitable processes have also been published in WO 97/49768.

Some of the siloxane compounds (V) are commercially available, or they can be obtained according to methods known to the person skilled in the art. For example, preparation methods and literature references for preparation can be found in the catalogue of the Geleste company, "ABCR Geleste 2000", pages 434–447.

The photoinitiators are used according to the invention in the curing of free-radically polymerisable systems, with the aim of obtaining a cured surface having excellent properties. A crucial factor is that the photoinitiator concentrates at the surface of the formulation to be cured. As explained above, this is achieved by providing suitable substituents on the photoinitiator. Improved surface properties can be obtained using such initiators not only in purely photocurable systems, but also in mixed thermocurable/photocurable formulations. The present invention accordingly relates also to the use of photoinitiators of formula I in purely photocurable formulations and also to the use of photoinitiators of formula I in mixed photochemically and thermally curable formulations. Thermal curing can be effected before, during or after the irradiation.

The invention accordingly relates also to a process as described above, in which the photocurable formulation comprises as further component at least one thermally crosslinkable compound (C), and the curing of the formulation is carried out by irradiation with light of a wavelength of from 200 to 600 nm and by prior, simultaneous and/or subsequent action of heat.

According to the invention the compounds of formula I may be used as surface-active photoinitiators for the photopolymerisation of ethylenically unsaturated compounds or mixtures comprising such compounds, and become oriented towards the surface of the formulation in question. According to the invention the initiators of formula (I) are not used in compositions that contain siloxane-modified resin components since concentration at the surface cannot occur therein, but instead the initiators are compatible with the formulation and are therefore readily miscible or compatible therewith.

The photoinitiators can also be used in combination with other photoinitiators (E) and/or further additives (D).

The invention accordingly relates also to photopolymerisable compositions, comprising (A) at least one ethylenically unsaturated free-radically photopolymerisable compound; and (B) at least one surface-active photoinitiator of formula I, provided that the composition does not contain any siloxane-modified resins in addition to the photoinitiator.

The invention relates also to photopolymerisable compositions, comprising (A) at least one ethylenically unsaturated free-radically photopolymerisable compound;

(B) at least one surface-active photoinitiator of formula I, and (C) at least one thermally crosslinkable compound; provided that the composition does not contain any siloxane-modified resins in addition to the photoinitiator.

According to the invention, the compositions may also comprise further different photoinitiators (E) and/or further additives (D).

It is also possible to add catalysts for the thermal crosslinking. Suitable examples are listed below.

The unsaturated compounds (A) may contain one or more olefinic double bonds. They may be low molecular weight (monomeric) or higher molecular weight (oligomeric). Examples of monomers having a double bond are alkyl and hydroxyalkyl acrylates and methacrylates, such as methyl, ethyl, butyl, 2-ethylhexyl and 2-hydroxyethyl acrylate, isobornyl acrylate and methyl and ethyl methacrylate. Further examples thereof are acrylonitrile, acrylamide, methacrylamide, N-substituted (meth)acrylamides, vinyl esters, such as vinyl acetate, vinyl ethers, such as isobutyl vinyl ether, styrene, alkyl- and halo-styrenes, N-vinylpyrrolidone, vinyl chloride and vinylidene chloride.

Examples of monomers having several double bonds are ethylene glycol diacrylate, propylene glycol diacrylate, neopentyl glycol diacrylate, hexamethylene glycol diacrylate and bisphenol A diacrylate, 4,4'-bis(2-acryloyloxyethoxy) diphenylpropane, trimethylolpropane tri-acrylate, pentaerythritol triacrylate or tetraacrylate, vinyl acrylate, divinyl benzene, divinyl succinate, diallyl phthalate, triallyl phosphate, triallyl isocyanurate and tris(2-acryloylethyl) isocyanurate.

Examples of higher molecular weight (oligomeric) polyunsaturated compounds are acrylated epoxy resins, acrylated or vinyl-ether- or epoxy-group-containing polyesters, polyurethanes and polyethers. Further examples of unsaturated oligomers are unsaturated polyester resins, which are usually prepared from maleic acid, phthalic acid and one or more diols and have molecular weights of approximately from 500 to 3000. Vinyl ether monomers and oligomers, and maleate-terminated oligomers having polyester, polyurethane, polyether, polyvinyl ether and epoxy main chains can also be used. In particular, combinations of vinyl-ether-group-carrying oligomers and polymers, as described in WO 90/01512, are very suitable. Also suitable are copolymers of monomers functionalised with vinyl ether and maleic acid. Such unsaturated oligomers can also be referred to as prepolymers.

Functionalised acrylates are also suitable. Examples of suitable monomers that are normally used to form the backbone (the base polymer) of such functionalised acrylate and methacrylate polymers are, for example, acrylate, methacrylate, methyl methacrylate, ethyl acrylate, ethyl methacrylate, n-butyl acrylate, n-butyl methacrylate, isobutyl acrylate, isobutyl methacrylate, 2-ethylhexyl acrylate, 2-ethylhexyl methacrylate, etc. In addition, suitable amounts of functional monomers are copolymerised during the polymerisation so as to obtain the functional polymers. Acid-functionalised acrylate or methacrylate polymers are obtained using acid-functional monomers, such as acrylic acid and methacrylic acid. Hydroxy-functional acrylate or methacrylate polymers are produced from hydroxy-functional monomers, such as 2-hydroxyethyl methacrylate, 2-hydroxypropyl methacrylate and 3,4-dihydroxybutyl methacrylate. Epoxy-functionalised acrylate or methacrylate polymers are obtained using epoxy-functional monomers, such as glycidyl methacrylate, 2,3-epoxybutyl methacrylate, 3,4-epoxybutyl methacrylate, 2,3-epoxycyclohexyl methacrylate, 10,11-epoxyundecyl methacrylate, etc. It is also possible to prepare e.g. isocyanate-functionalised polymers from isocyanate-functionalised monomers, such as meta-isopropenyl-$\alpha,\alpha$-dimethylbenzyl isocyanate.

Especially suitable are, for example, esters of ethylenically unsaturated mono- or poly-functional carboxylic acids and polyols or polyepoxides, and polymers having ethylenically unsaturated groups in the chain or in side groups, such as unsaturated polyesters, polyamides and polyurethanes and copolymers thereof, alkyd resins, polybutadiene and butadiene copolymers, polyisoprene and isoprene copolymers, polymers and copolymers having (meth)acrylic groups in side chains, and mixtures of one or more such polymers.

Examples of suitable mono- or poly-functional unsaturated carboxylic acids are acrylic acid, methacrylic acid, crotonic acid, itaconic acid, cinnamic acid, maleic acid and fumaric acid and unsaturated fatty acids, such as linolenic acid or oleic acid. Preference is given to acrylic acid and methacrylic acid.

Saturated di- or poly-carboxylic acids in admixture with unsaturated carboxylic acids may, however, also be used. Examples of suitable saturated di- or poly-carboxylic acids include, for example, tetrachlorophthalic acid, tetrabromophthalic acid, phthalic acid anhydride, adipic acid, tetrahydrophthalic acid, isophthalic acid, terephthalic acid, trimellitic acid, heptanedicarboxylic acid, sebacic acid, dodecanedicarboxylic acid, hexahydrophthalic acid, etc.

Suitable polyols are aromatic and especially aliphatic and cycloaliphatic polyols. Examples of aromatic polyols are hydroquinone, 4,4'-dihydroxydiphenyl, 2,2-di(4-hydroxyphenyl)-propane, and novolaks and resoles. Examples of polyepoxides are those based on the polyols mentioned, especially the aromatic polyols and epichlorohydrin. Also suitable as polyols are polymers and copolymers containing hydroxyl groups in the polymer chain or in side groups, such as polyvinyl alcohol and copolymers thereof or polymethacrylic acid hydroxyalkyl esters or copolymers thereof. Further suitable polyols are oligoesters having hydroxyl terminal groups.

Examples of aliphatic and cycloaliphatic polyols are alkylenediols having preferably from 2 to 12 carbon atoms, such as ethylene glycol, 1,2- or 1,3-propanediol, 1,2-, 1,3- or 1,4-butanediol, pentanediol, hexanediol, octanediol, dodecanediol, diethylene glycol, triethylene glycol, polyethylene glycols having molecular weights of preferably from 200 to 1500, 1,3-cyclopentanediol, 1,2-, 1,3- or 1,4-cyclohexanediol, 1,4-dihydroxymethylcyclohexane, glycerol, tris($\beta$-hydroxy-ethyl)amine, trimethylolethane, trimethylolpropane, pentaerythritol, dipentaerythritol and sorbitol.

The polyols may be partially or fully esterified by one or by different unsaturated carboxylic acid(s), it being possible for the free hydroxyl groups in partial esters to have been modified, for example etherified, or esterified with other carboxylic acids.

Examples of esters are: trimethylolpropane triacrylate, trimethylolethane triacrylate, trimethylolpropane trimethacrylate, trimethylolethane trimethacrylate, tetramethylene glycol dimethacrylate, triethylene glycol dimethacrylate, tetraethylene glycol diacrylate, pentaerythritol diacrylate, pentaerythritol triacrylate, pentaerythritol tetraacrylate, dipentaerythritol diacrylate, dipentaerythritol triacrylate, dipentaerythritol tetraacrylate, dipentaerythritol pentaacrylate, dipentaerythritol hexaacrylate, tripentaerythritol octaacrylate, pentaerythritol dimethacrylate, pentaerythritol trimethacrylate, dipentaerythritol dimethacrylate, dipentaerythritol tetramethacrylate, tripentaerythritol octamethacrylate, pentaerythritol diitaconate, dipentaerythritol trisitaconate, dipentaerythritol pentaitaconate, dipentaerythritol hexaitaconate, ethylene glycol diacrylate, 1,3-butanediol diacrylate, 1,3-butanediol dimethacrylate, 1,4-butanediol diitaconate, sorbitol triacrylate, sorbitol tetraacrylate, pentaerythritol-modified triacrylate, sorbitol tetramethacrylate, sorbitol pentaacrylate, sorbitol hexaacrylate, oligo-ester acrylates and methacrylates, glycerol di- and tri-acrylate, 1,4-cyclohexane diacrylate, bisacrylates and bismethacrylates of polyethylene glycol having a molecular weight of from 200 to 1500, and mixtures thereof.

Suitable components (A) are also the amides of identical or different unsaturated carboxylic acids and aromatic, cycloaliphatic and aliphatic polyamines having preferably from 2 to 6, especially from 2 to 4, amino groups. Examples of such polyamines are ethylenediamine, 1,2- or 1,3-propylenediamine, 1,2-, 1,3- or 1,4-butylenediamine, 1,5-pentylenediamine, 1,6-hexylenediamine, octylenediamine, dodecylenediamine, 1,4-diaminocyclohexane, isophoronediamine, phenylenediamine, bisphenylenediamine, di-$\beta$-aminoethyl ether, diethylenetriamine, triethylenetetraamine and di($\beta$-aminoethoxy)- or di($\beta$-aminopropoxy)ethane. Further suitable polyamines are polymers and copolymers which may have additional amino groups in the side chain and oligoamides having amino terminal groups. Examples of such unsaturated amides are: methylene bisacrylamide, 1,6-hexamethylene bisacrylamide, diethylenetriamine trismethacrylamide, bis(methacrylamidopropoxy)ethane, $\beta$-methacrylamidoethyl methacrylate and N-[($\beta$-hydroxyethoxy)ethyl]-acrylamide.

Suitable unsaturated polyesters and polyamides are derived, for example, from maleic acid and diols or diamines. The maleic acid may have been partially replaced by other dicarboxylic acids. They can be used together with ethylenically unsaturated comonomers, for example styrene. The polyesters and polyamides can also be derived from dicarboxylic acids and ethylenically unsaturated diols or diamines, especially from those having longer chains of, for example, from 6 to 20 carbon atoms. Examples of polyurethanes are those composed of saturated diisocyanates and unsaturated diols, or unsaturated diisocyanates and saturated diols.

Polybutadiene and polyisoprene and copolymers thereof are known. Suitable comonomers include, for example, olefins, such as ethylene, propene, butene, hexene, (meth) acrylates, acrylonitrile, styrene and vinyl chloride. Polymers having (meth)acrylate groups in the side chain are also known. They may be, for example, reaction products of novolak-based epoxy resins with (meth)acrylic acid; homo- or co-polymers of vinyl alcohol or hydroxyalkyl derivatives thereof that have been esterified with (meth)acrylic acid; or homo- and co-polymers of (meth)acrylates that have been esterified with hydroxyalkyl (meth)acrylates.

The photopolymerisable compounds (A) may be used on their own or in any desired mixtures. Preference is given to mixtures of polyol (meth)acrylates.

Binders may also be added to the compositions according to the invention, this being especially advantageous when the photopolymerisable compounds are liquid or viscous substances. The amount of binder may be, for example, from 5 to 95% by weight, preferably from 10 to 90% by weight and especially from 40 to 90% by weight, based on total solids. The binder will be selected according to the field of use and the properties required therefor, such as developability in aqueous and organic solvent systems, adhesion to substrates and sensitivity to oxygen.

Suitable binders are, for example, polymers having a molecular weight of approximately from 5000 to 2,000,000, preferably from 10,000 to 1,000,000. Examples thereof are: homo- and co-polymers of acrylates and methacrylates, for example copolymers of methyl meth-acrylate/ethyl acrylate/ methacrylic acid, poly(methacrylic acid alkyl esters), poly (acrylic acid alkyl esters); cellulose esters and ethers, such as cellulose acetate, cellulose acetate butyrate, methyl cellulose, ethyl cellulose; polyvinyl butyral, polyvinylformal, cyclised rubber, polyethers, such as polyethylene oxide, polypropylene oxide, polytetrahydrofuran; polystyrene, polycarbonate, polyurethane, chlorinated polyolefins, polyvinyl chloride, copolymers of vinyl chloride/vinylidene chloride, copolymers of vinylidene chloride with acrylonitrile, methyl methacrylate and vinyl acetate, polyvinyl acetate, copoly(ethylene/vinyl acetate), polymers such as polycaprolactam and poly (hexamethyleneadipamide), polyesters such as poly (ethylene glycol terephthalate) and poly(hexamethylene glycol succinate).

The resins mentioned below under (C1) may also be used as component (A), that is to say as UV-curable component. Of particular interest are, for example, unsaturated acrylates having reactive functional groups. The reactive functional group may be selected, for example, from a hydroxyl, thiol, isocyanate, epoxy, anhydride, carboxyl, amino or blocked amino group. Examples of OH-group-containing unsaturated acrylates are hydroxyethyl and hydroxybutyl acrylates and also glycidyl acrylates.

The unsaturated compounds may also be used in admixture with non-photopolymerisable film-forming components. These may be, for example, polymers that can be dried physically or solutions thereof in organic solvents, such as nitrocellulose or cellulose acetobutyrate. They may alternatively be chemically or thermally curable resins, such as polyisocyanates, polyepoxides or melamine resins. The concomitant use of thermally curable resins is important for use in so-called hybrid systems which are both photopolymerised and thermally crosslinked.

Component (A) may, for example, be a coating composition comprising
(A1) compounds having one or more free-radically polymerisable double bonds that additionally contain at least one further functional group that is reactive in terms of an addition and/or condensation reaction (examples are given above),
(A2) compounds having one or more free-radically polymerisable double bonds that additionally contain at least one further functional group that is reactive in terms of an addition and/or condensation reaction, the additional reactive functional group being complementary or reactive towards the additional reactive functional groups of component (A1),
(A3) optionally at least one monomeric, oligomeric and/ or polymeric compound having at least one functional group that is reactive in terms of an addition and/or condensation reaction towards the functional groups of component (A1) or component (A2) that are present in addition to the free-radically polymerisable double bonds.

Component (A2) in each case carries the groups complementary or reactive towards component (A1). Different types of functional groups may also be present in a component. Component (A3) provides a further component that contains functional groups that are reactive in terms of an addition and/or condensation reaction and that are able to react with the functional groups of (A1) or (A2) that are present in addition to the free-radically polymerisable double bonds. Component (A3) contains no free-radically polymerisable double bonds. Examples of such combinations (A1), (A2), (A3) can be found in WO 99/55785.

Examples of suitable reactive functional groups are selected, for example, from hydroxyl, isocyanate, epoxy, anhydride, carboxyl and blocked amino groups. Examples have been described above.

Constituents of component (C) are, for example, thermally curable lacquer or coating system constituents customary in the art. Component (C) accordingly may consist of a number of constituents.

Examples of component (C) are, for example, oligomers and/or polymers derived from α,β-unsaturated acids and derivatives thereof, for example polyacrylates and polymethacrylates, polymethyl methacrylates impact-resistant-modified with butyl acrylate, polyacrylamides and polyacrylonitriles. Further examples of component (C) are urethanes, polyurethanes derived from on the one hand polyethers, polyesters and polyacrylates having free hydroxyl groups and on the other hand aliphatic or aromatic polyisocyanates, and pre-products thereof. Component (C) accordingly also includes, for example, crosslinkable acrylic resins derived from substituted acrylic acid esters, for example epoxy acrylates, urethane acrylates and polyester acrylates. Alkyd resins, polyester resins and acrylate resins and modifications thereof that are crosslinked with melamine resins, urea resins, isocyanates, isocyanurates, polyisocyanates, polyisocyanurates and epoxy resins, may also be a constituent of component (C).

Component (C) is, for example, generally a film-forming binder based on a thermoplastic or thermocurable resin, predominantly on a thermocurable resin. Examples thereof are alkyd, acrylic, polyester, phenol, melamine, epoxy and polyurethane resins and mixtures thereof. Examples thereof are described, for example, in Ullmann's Encyclopedia of Industrial Chemistry, 5th Ed., Vol. A18, pp. 368–426, VCH, Weinheim 1991.

Component (C) may be a cold-curable or hot-curable binder, with the addition of a curing catalyst possibly being advantageous. Suitable catalysts that accelerate the full cure of the binder are described, for example, in Ullmann's Encyclopedia of Industrial Chemistry, Vol. A18, page 469, VCH Verlagsgesellschaft, Weinheim 1991.

Examples of specific binders suitable as component (C) are:
1. surface-coatings based on cold- or hot-crosslinkable alkyd, acrylate, polyester, epoxy or melamine resins or mixtures of such resins, optionally with the addition of a curing catalyst;

2. two-component polyurethane surface-coatings based on hydroxyl-group-containing acrylate, polyester or polyether resins and aliphatic or aromatic isocyanates, isocyanurates or polyisocyanates;
3. one-component polyurethane surface-coatings based on blocked isocyanates, isocyanurates or polyisocyanates, which are de-blocked during stoving; it is also possible to add melamine resins as appropriate;
4. one-component polyurethane surface-coatings based on aliphatic or aromatic urethanes or polyurethanes and hydroxyl-group-containing acrylate, polyester or polyether resins;
5. one-component polyurethane surface-coatings based on aliphatic or aromatic urethane acrylates or polyurethane acrylates having free amine groups in the urethane structure and melamine resins or polyether resins, optionally with the addition of a curing catalyst;
6. two-component surface-coatings based on (poly) ketimines and aliphatic or aromatic isocyanates, isocyanurates or polyisocyanates;
7. two-component surface-coatings based on (poly) ketimines and an unsaturated acrylate resin or a polyacetoacetate resin or a methacrylamidoglycolate methyl ester;
8. two-component surface-coatings based on carboxyl- or amino-groups-containing polyacrylates and polyepoxides;
9. two-component surface-coatings based on anhydride-group-containing acrylate resins and a polyhydroxy or polyamino component;
10. two-component surface-coatings based on acrylate-containing anhydrides and polyepoxides;
11. two-component surface-coatings based on (poly) oxazolines and anhydride-group-containing acrylate resins or unsaturated acrylate resins or aliphatic or aromatic isocyanates, isocyanurates or polyisocyanates;
12. two-component surface-coatings based on unsaturated polyacrylates and polymalonates;
13. thermoplastic polyacrylate surface-coatings based on thermoplastic acrylate resins or extrinsically crosslinking acrylate resins in combination with etherified melamine resins;
14. surface-coating systems based on urethane (meth) acrylate having (meth)acryloyl groups and free isocyanate groups and on one or more compounds that react with isocyanates, for example free or esterified polyols. Such systems have been published, for example, in EP 928800.

Blocked isocyanates, as may also be used in component (C), are described, for example, in Organischer Metallschutz: Entwicklung und Anwendung von Beschichtungsstoffen, pages 159–160, Vincentz Verlag, Hanover (1993). These are compounds in which the highly reactive NCO group is "blocked" by reaction with specific radicals, for example primary alcohols, phenol, acetoacetic ester, F-caprolactam, phthalimide, imidazole, oxime or amine. The blocked isocyanate is stable in liquid systems and also in the presence of hydroxy groups. Upon heating, the blocking agent is removed again and the NCO group is freed.

1-Component (1C) and 2-component (2C) systems may be used as component (C). Examples of such systems are described in Ullmann's Encyclopedia of Industrial Chemistry, Vol. A18, Paints and Coatings, pages 404–407, VCH Verlagsgesellschaft mbH, Weinheim (1991).

It is possible to optimise the composition by specially adapting the formulation, for example by varying the binder/crosslinking agent ratio. Such measures will be known to the person skilled in the art of surface-coating technology.

In the curing process according to the invention, component (C) is preferably a mixture based on acrylate/melamine (and melamine derivates), 2-component polyurethane, 1-component polyurethane, 2-component epoxy/carboxy or 1-component epoxy/carboxy. Mixtures of those systems are also possible, for example the addition of melamine (or derivatives thereof) to 1-component polyurethanes.

Component (C) is preferably a binder based on a polyacrylate with melamine or on a melamine derivative. Preference is also given to a system based on a polyacrylate and/or polyester polyol with an unblocked polyisocyanate or polyisocyanurate.

Component (C) may also comprise monomeric and/or oligomeric compounds having ethylenically unsaturated bonds (prepolymers) that additionally contain at least one or more OH, $NH_2$, COOH, epoxy or NCO groups (=C1) that are capable of reaction with the binder and/or the crosslinking agent constituent of component (C). After application and thermal curing, the ethylenically unsaturated bonds are converted to a crosslinked, high molecular weight form by UV radiation. Examples of such components (C) are described, for example, in the above-mentioned publication, Ullmann's Encyclopedia of Industrial Chemistry, 5th Ed., Vol. A18, pages 451–453, or by S. Urano, K. Aoki, N. Tsuboniva and R. Mizuguchi in Progress in Organic Coatings, 20 (1992), 471–486, or by H. Terashima and O. Isozaki in JOCCA 1992 (6), 222.

(C1) may, for example, be an OH-group-containing unsaturated acrylate, for example hydroxyethyl or hydroxybutyl acrylate or a glycidyl acrylate. Component (C1) may be of any desired structure (for example it may contain units of polyester, polyacrylate, polyether, etc.), provided that it contains an ethylenically unsaturated double bond and additionally free OH, COOH, $NH_2$, epoxy or NCO groups.

(C1) may, for example, also be obtained by reacting an epoxy-functional oligomer with acrylic acid or methacrylic acid. A typical example of an OH-functional oligomer having vinylic double bonds is

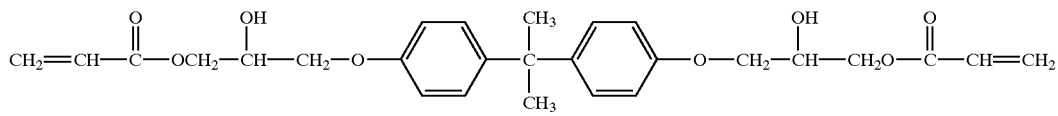

obtained by reaction of

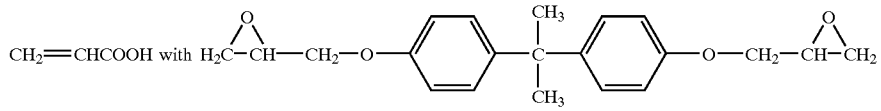

Another possible method of preparing component ($C_1$) is, for example, the reaction of an oligomer that contains only one epoxy group and has a free OH group at another position in the molecule.

The quantity ratio of components (A) to (C) in the UV- and thermally-crosslinking formulations is not critical. "Dual-cure" systems are known to the person skilled in the art, who will therefore be familiar with the optimum ratios of the UV- and thermally-crosslinkable components for a particular desired use. For example, compositions may contain components (A) and (C), for example, in a ratio of from 5:95 to 95:5, from 20:80 to 80:20 or from 30:70 to 70:30, for example from 40:60 to 60:40.

Examples of "dual-cure" systems, that is to say systems comprising both UV-curable and thermally curable components, can be found inter alia in U.S. Pat. No. 5,922,473, columns 6 to 10.

It is also possible to add solvent or water to the compositions used in the process according to the invention. If the compositions are used without solvent, they are, for example, powder coating formulations. Suitable solvents are solvents known to the person skilled in the art, especially those customary in surface-coating technology. Examples thereof are various organic solvents, such as ketones, for example methyl ethyl ketone, cyclohexanone; aromatic hydrocarbons, for example toluene, xylene and tetramethylbenzene; glycol ethers, such as diethylene glycol monoethyl ether, dipropylene glycol diethyl ether; esters, for example ethyl acetate; aliphatic hydrocarbons, such as hexane, octane, decane; and petroleum solvents, for example petroleum ether.

The compounds and mixtures thereof according to the invention may also be used as free-radical photoinitiators or photoinitiating systems for radiation-curable powder coating compositions. The powder coating compositions may be based on solid resins and monomers containing reactive double bonds, for example maleates, vinyl ethers, acrylates, acryl-amides and mixtures thereof. A free-radically UV-curable powder coating composition can be formulated by mixing unsaturated polyester resins with solid acrylamides (for example methylacrylamidoglycolate methyl ester) and a free-radical photoinitiator according to the invention, as described, for example, in the presentation "Radiation Curing of Powder Coating", Conference Proceedings, Radtech Europe 1993 by M. Wittig and Th. Gohmann. Free-radically UV-curable powder coating compositions can also be formulated by mixing unsaturated polyester resins with solid acrylates, methacrylates or vinyl ethers and a photoinitiator (or photoinitiator mixture) according to the invention. The powder coating compositions may also comprise binders, as described, for example, in DE 4228514 and EP 636669. The powder coating formulations described in EP 636669 comprise, for example, a) an unsaturated resin from the group of (semi)crystalline or amorphous unsaturated polyesters, unsaturated polyacrylates or mixtures thereof with unsaturated polyesters, special preference being given to those derived from maleic acid or fumaric acid; b) an oligomeric or polymeric crosslinking agent having vinyl ether-, vinyl ester- or (meth)acrylate-functional groups, special preference being given to vinyl ether oligomers, such as divinyl-ether-functionalised urethanes; c) the photoinitiator.

The UV-curable powder coating compositions may also comprise white or coloured pigments. Thus, for example, especially rutile titanium dioxide can be used in concentrations of up to 50% by weight in order to obtain a cured powder coating having good covering power. The process normally comprises spraying the powder electrostatically or tribostatically onto the substrate, for example metal or wood, melting the powder by heating and, once a smooth film has been produced, radiation-curing the coating with ultraviolet and/or visible light, for example using medium-pressure mercury lamps, metal halide lamps or xenon lamps. A particular advantage of radiation-curable powder coating compositions over corresponding thermally curable powder coating compositions is that the flow time after the powder particles have been melted can be prolonged as desired to ensure the formation of a smooth high-gloss coating. Unlike thermally curable systems, radiation-curable powder coating compositions can be so formulated that they melt at relatively low temperatures, without the undesirable effect of their useful life being shortened. For that reason they are also suitable as coatings for heat-sensitive substrates, such as wood or plastics.

If the powder coating compositions are to be applied to substrates that are not heat-sensitive, for example to metals (automotive coatings), it is also possible to provide "dual cure" powder coating formulations using the photoinitiators according to the invention. Such formulations are known to the person skilled in the art and are both thermally cured and UV-cured. Such formulations can be found, for example, in U.S. Pat. No. 5,922,473.

The powder coating formulations may also comprise UV-absorbers in addition to the photoinitiators according to the invention. Suitable examples thereof are listed below.

The photopolymerisable mixtures may comprise various additives (D) in addition to the photoinitiator. Examples thereof are thermal inhibitors, the purpose of which is to prevent pre-mature polymerisation, for example hydroquinone, hydroquinone derivatives, p-methoxyphenol, β-naphthol and sterically hindered phenols, for example 2,6-di(tert-butyl)-p-cresol. In order to increase stability to dark storage, it is possible, for example, to use copper compounds, such as copper naphthenate, stearate or octoate, phosphorus compounds, for example triphenylphosphine, tributylphosphine, triethyl phosphite, triphenyl phosphite or tribenzyl phosphite, quaternary ammonium compounds, for example tetramethylammonium chloride or trimethylbenzylammonium chloride, or hydroxylamine derivatives, for example N-diethylhydroxylamine. In order to exclude atmospheric oxygen during polymerisation, it is possible to add paraffin or similar wax-like substances that, being insufficiently soluble in the polymer, migrate to the surface at the beginning of the polymerisation and form a transparent surface layer which prevents the ingress of air. Equally possible is the application of an oxygen-impermeable layer. UV-Absorbers, for example of the hydroxyphenyl-benzotriazole, hydroxyphenyl-benzophenone, oxalic acid amide or hydroxyphenyl-s-triazine type, may be added as light stabilisers. Individual compounds or mixtures of those compounds may be used with or without the use of sterically hindered amines (HALS).

Examples of such UV-absorbers and light stabilisers are
1. 2-(2'-Hydroxyphenyl)benzotriazoles, for example 2-(2'-hydroxy-5'-methylphenyl)benzotriazole, 2-(3',5'-di-tert-butyl-2'-hydroxyphenyl)benzotriazole, 2-(5'-tert-butyl-2'-hydroxy-phenyl)benzotriazole, 2-(2'-hydroxy-5'-(1,1,3,3-tetramethylbutyl)phenyl) benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl)benzo-triazole, 2-(2'-hydroxy-4'-octyloxyphenyl)benzotriazole, 2-(3',5'-di-tert-amyl-2'-hydroxy-phenyl)benzotriazole, 2-(3',5'- bis-(α,α-dimethylbenzyl)-2'-hydroxyphenyl) benzotriazole, 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl)phenyl)-5-chloro-benzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl) phenyl)benzotriazole, 2-(3'-tert-butyl-5'-[2-(2-ethylhexyl-oxy)carbonylethyl]-2'-hydroxyphenyl) benzotriazole, 2-(3'-dodecyl-2'-hydroxy-5'-methyl-phenyl)benzotriazole, 2-(3'-tert-butyl-2'-hydroxy-5'-(2-isooctyloxycarbonylethyl)-phenyl-benzotriazole, 2,2'-methylene-bis[4-(1,1,3,3-tetramethylbutyl)-6-benzotriazol-2-yl-phenol]; the transesterification product of 2-[3'-tert-butyl-5'-(2-methoxycarbonylethyl)-2'-hydroxyphenyl]-2H-benzotriazole with polyethylene glycol 300; [R—CH₂CH₂—COO—CH₂CH₂]₂— where R=3'-tert-butyl-4'-hydroxy-5'-2H-benzotriazol-2-ylphenyl, 2-[2'-hydroxy-3'-(α,α-dimethylbenzyl)-5'-(1,1,3,3-tetramethylbutyl)-phenyl]benzotriazole; 2-[2'-hydroxy-3'-(1,1,3,3-tetramethylbutyl)-5'-(α,α-dimethylbenzyl)-phenyl]benzotriazole.
2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.
3. Esters of substituted and unsubstituted benzoic acids, as for example 4-tert-butyl-phenyl salicylate, phenyl salicylate, octylphenyl salicylate, dibenzoyl resorcinol, bis(4-tert-butylbenzoyl) resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.
4. Acrylates, for example ethyl α-cyano-β,β-diphenylacrylate, isooctyl α-cyano-β,β-diphenylacrylate, methyl α-methoxycarbonylcinnamate, methyl α-cyano-β-methyl-p-methoxy-cinnamate, butyl α-cyano-β-methyl-p-methoxy-cinnamate, methyl α-methoxycarbonyl-p-methoxy-cinnamate and N-(β-methoxycarbonyl-β-cyanovinyl)-2-methylindoline.
5. Sterically hindered amines, for example bis(2,2,6,6-tetramethyl-4-piperidyl)sebacate, bis-(2,2,6,6-tetramethyl-4-piperidyl)succinate, bis(1,2,2,6,6-pentamethyl-4-piperidyl)-sebacate, bis(1-octyloxy-2,2,6,6-tetramethyl-4-piperidyl)sebacate, bis(1,2,2,6,6-penta-methyl-4-piperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidyl)hexamethylenediamine and 4-tert-octylamino-2,6-dichloro-1,3,5-triazine, tris(2,2,6,6-tetramethyl-4-piperidyl)nitrilotriacetate, tetrakis(2,2,6, 6-tetramethyl-4-piperidyl)-1,2,3,4-butane-tetracarboxylate, 1,1'-(1,2-ethane-diyl)-bis(3,3,5,5-tetramethylpiperazinone), 4-benzoyl-2,2,6,6-tetramethylpiperidine, 4-stearyl-oxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro-[4.5]decane-2,4-dione, bis(1-octyloxy-2,2,6,6-tetramethylpiperidyl)sebacate, bis(1-octyloxy-2,2,6,6-tetramethylpiperidyl)succinate, linear or cyclic condensates of N,N'-bis-(2,2,6,6-tetramethyl-4-piperidyl)hexamethylenediamine and 4-morpholino-2,6-dichloro-1,3,5-triazine, the condensate of 2-chloro-4,6-bis-(4-n-butylamino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis(3-aminopropyl-amino)ethane, 8-acetyl-3-dodecyl-7,7,9, 9-tetramethyl-1,3,8-triazaspiro[4.5]decane-2,4-dione, 3-dodecyl-1-(2,2,6,6-tetramethyl-4-piperidyl) pyrrolidine-2,5-dione, 3-dodecyl-1-(1,2,2,6,6-pentamethyl-4-piperidyl)pyrrolidine-2,5-dione, a mixture of 4-hexadecyloxy- and 4-stearyloxy-2,2,6,6-tetramethylpiperidine, a condensation product of N,N'-bis(2,2,6,6-tetramethyl-4-piperidyl) hexamethylenediamine and 4-cyclohexylamino-2,6-dichloro-1,3,5-triazine, a condensation product of 1,2-bis(3-aminopropylamino)ethane and 2,4,6-trichloro-1, 3,5-triazine as well as 4-butylamino-2,2,6,6-tetramethylpiperidine (CAS Reg. No. [136504-96-6]); N-(2,2,6,6-tetramethyl-4-piperidyl)-n-dodecylsuccinimide, N-(1,2,2,6,6-pentamethyl-4-piperidyl)-n-dodecylsuccinimide, 2-undecyl-7,7,9,9-tetramethyl-1-oxa-3,8-diaza-4-oxo-spiro[4,5]decane, a reaction product of 7,7,9,9-tetramethyl-2-cycloundecyl-1-oxa-3,8-diaza-4-oxospiro[4,5]decane and epichlorohydrin, 1,1-bis(1,2,2,6,6-pentamethyl-4-piper-idyloxycarbonyl)-2-(4-methoxyphenyl)ethene, N,N'-bis-formyl-N,N'-bis(2,2,6,6-tetra-methyl-4-piperidyl)hexamethylenediamine, diester of 4-methoxy-methylene-malonic acid with 1,2,2,6,6-pentamethyl-4-hydroxypiperidine, poly[methylpropyl-3-oxy-4-(2,2,6,6-tetramethyl-4-piperidyl)]siloxane, reaction product of maleic acid anhydride-a-olefin-copolymer with 2,2,6,6-tetramethyl-4-aminopiperidine or 1,2,2,6,6-pentamethyl-4-aminopiperidine.
6. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.
7. 2-(2-Hydroxyphenyl)-1,3,5-triazines, for example 2,4, 6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyl-oxyphenyl)-6-(2, 4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2, 4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxy-propoxy)phenyl]-4,6-bis(2,4-dimethyl)-1,3,5-triazine, 2-[2-hydroxy-4-(2-hydroxy-3-octyloxy-propyloxy) phenyl]-4,6-bis(2,4-dimethyl)-1,3,5-triazine, 2-[4-(dodecyloxy/tridecyloxy-2-hydroxypropoxy)-2-hydroxy-phenyl]-4,6-bis(2,4-dimethyl-phenyl)-1,3,5-triazine, 2-[2-hydroxy-4-(2-hydroxy-3-dodecyloxypropoxy)phenyl]-4,6-bis(2,4-dimethylphenyl)-1,3,5-triazine, 2-(2-hydroxy-4-hexyloxy)phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxy-propoxy)phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxypropyloxy]phenyl}-4,6-bis(2,4-dimethylphenyl)-1,3,5-triazine.

8. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, bis(2,6-di-tert-butyl-4-methylphenyl)-pentaerythritol diphosphite, diisodecyloxypentaerythritol diphosphite, bis(2,4-di-tert-butyl-6-methylphenyl)pentaerythritol diphosphite, bis(2,4,6-tris(tert-butyl-phenyl) pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenz-[d,g]-1,3,2-dioxaphosphocine, bis(2,4-di-tert-butyl-6-methylphenyl) methyl phosphite, bis(2,4-di-tert-butyl-6-methylphenyl) ethyl phosphite, 6-fluoro-2,4,8,10-tetra-tert-butyl-12-methyl-dibenz[d,g]-1,3,2-dioxaphosphocine, 2,2',2"-nitrilo[triethyltris(3,3',5,5'-tetra-tert-butyl-1,1'-biphenyl-2,2'-diyl)phosphite], 2-ethylhexyl(3,3',5,5'-tetra-tert-butyl-1,1'-biphenyl-2,2'-diyl)phosphite, 5-butyl-5-ethyl-2-(2,4,6-tri-tert-butylphenoxy)-1,3,2-dioxaphosphirane.

Additives customary in the art, such as antistatics, flow improvers, levelling agents and adhesion promoters, may also be used.

The photoinitiators of formula I provided with siloxane radicals can also serve as flow improvers since they are oriented towards the surface and influence the surface properties by way of the siloxane radical. It is also possible to add further flow improvers customary in the art. Examples thereof are siloxane compounds and fluorohydrocarbon compounds, such as are widely available commercially.

The invention relates also to the use of compounds of formula I as flow improvers, optionally in combination with other customary flow improvers.

Flow is defined, according to DIN 55945, as "the ability, to a greater or lesser degree, of a still liquid paint to level out, by itself, any unevenness arising during its application" (see J. Bielemann, Lackadditive, VCH Weinheim 1998, Chapter 6). The flow of a coating composition is highly dependent upon its flow behaviour and its surface tension. The term "flow improver" is used to denote a substance that, by lowering the viscosity and/or the surface tension, enables wet coatings to become evenly flowing films. In the case of powder coating compositions, flow improvers also lower the melt viscosity and the glass transition temperature, and they also act as de-gassing agents. The use of flow improvers eliminates flow and surface faults that impair the overall appearance of the coating. Flow and surface faults include, inter alia, orange peel effect, structure formation, scratching, fisheye formation, sensitivity to draught, substrate wetting problems, brush application marks, run formation, stippling, pinholes, etc. The use of the compounds according to the invention as flow improvers enables the surface tension to be lowered. The surface tension can be calculated by determining the wetting angle of a drop of liquid on a surface (contact angle measurement).

In order to accelerate the photopolymerisation it is possible to add as further additives (D) amines, for example triethanolamine, N-methyl-diethanolamine, p-dimethylaminobenzoic acid ethyl ester or Michler's ketone. The action of the amines can be enhanced by the addition of aromatic ketones of the benzophenone type. Amines that can be used as oxygen capture agents are, for example, substituted N,N-dialkylanilines, as described in EP 339841. Further accelerators, co-initiators and auto-oxidizers are thiols, thio ethers, disulfides and phosphines, as described, for example, in EP 438123 and GB 2180358.

It is also possible to add to the compositions according to the invention chain-transfer reagents customary in the art, examples of which are mercaptans, amines and benzothiazole.

Photopolymerisation can also be accelerated by adding as further additives (D) photosensitisers that shift or broaden the spectral sensitivity. These include especially aromatic carbonyl compounds, such as benzophenone and thioxanthone, especially also isopropylthioxanthone, anthraquinone and 3-acylcoumarin derivatives, terphenyls, styryl ketones, and 3-(aroylmethylene)-thiazolines, camphorquinone, and also eosin, rhodamine and erythrosine dyes.

The above-mentioned amines may, for example, also be regarded as photosensitisers.

The curing process, especially in the case of pigmented compositions (for example compositions pigmented with titanium dioxide) may also be assisted by the use of an additional additive (D) that is a component that forms free radicals under thermal conditions, for example an azo compound, such as 2,2'-azobis(4-methoxy-2,4-dimethylvaleronitrile), a triazene, diazo-sulfide, pentaazadiene or a peroxy compound, such as a hydrogen peroxide or peroxycarbonate, for example tert-butyl hydroperoxide, as described, for example, in EP 245639.

The compositions may also comprise as further additives (D), for example, a photoreducible dye, for example xanthene, benzoxanthene, benzothioxanthene, thiazine, pyronine, porphyrin or acridine dyes, and/or a radiation-cleavable trihalomethyl compound. Similar compositions are described, for example, in EP 445624.

Further customary additives (D) are—depending upon the intended use—optical brighteners, fillers, for example kaolin, talcum, barytes, gypsum, chalk or silicate-like fillers, pigments, dyes, wetting agents and flow improvers.

For the curing of thick and pigmented coatings it is suitable to add glass microbeads or pulverised glass fibres, as described, for example, in U.S. Pat. No. 5,013,768.

The formulations may also comprise colourants and/or white or coloured pigments. Depending upon the intended use, both inorganic and organic pigments may be used. Such additives are known to the person skilled in the art; some examples thereof are titanium dioxide pigments, for example of the rutile or anatase type, carbon black, zinc oxide, such as zinc white, iron oxides, such as iron oxide yellow, iron oxide red, chromium yellow, chromium green, nickel titanium yellow, ultramarine blue, cobalt blue, bismuth vanadate, cadmium yellow and cadmium red. Examples of organic pigments are mono- and bis-azo pigments, and metal complexes thereof, phthalocyanine pigments, polycyclic pigments, such as perylene, anthraquinone, thioindigo, quinacridone and triphenylmethane pigments, and diketo-pyrrolo-pyrrole, isoindolinone, for example tetrachloroisoindolinone, isoindoline, dioxazine, benzimidazolone and quinophthalone pigments.

The pigments may be used individually or in admixture in the formulations. Depending upon the intended use, the pigments are added to the formulations in amounts customary in the art, for example in an amount of from 1 to 60% by weight, or from 10 to 30% by weight, based on the total weight.

The formulations may, for example, also comprise organic colourants of a wide variety of classes, examples of which are azo dyes, methine dyes, anthraquinone dyes and metal complex dyes. Customary concentrations are, for example, from 0.1 to 20%, especially from 1 to 5%, based on the total weight.

The choice of additives will depend upon the field of use in question and upon the properties desired for that field. The additives (D) described above are customary in the art and are accordingly used in amounts customary in the art.

In certain cases it may be advantageous to use mixtures of two or more of the photoinitiators of formula I; for example it is advantageous to use mixtures formed directly during preparation. It is, of course, also possible to use mixtures with known photoinitiators (E), for example mixtures with camphorquinone, benzophenone, benzophenone derivatives, acetophenone, acetophenone derivatives, such as α-hydroxycycloalkylphenylketones or 2-hydroxy-2-methyl-1-phenyl-propanone, dialkoxyacetophenones, α-hydroxy- or α-amino-acetophenones, for example (4-methylthiobenzoyl)-1-methyl-1-morpholino-ethane, (4-morpholino-benzoyl)-1-benzyl-1-dimethylamino-propane, 4-aroyl-1,3-dioxolanes, benzoin alkyl ethers and benzil ketals, for example benzil dimethyl ketal, phenyl glyoxalates and derivatives thereof, dimeric phenyl glyoxalates, peresters, for example benzophenone tetracarboxylic acid peresters, as described, for example, in EP 126541, monoacylphosphine oxides, for example (2,4,6-trimethylbenzoyl)-phenyl-phosphine oxide, bisacylphosphine oxides, for example bis(2,6-dimethoxybenzoyl)-(2,4,4-trimethyl-pent-1-yl)phosphine oxide, bis(2,4,6-trimethylbenzoyl)-phenyl-phosphine oxide or bis(2,4,6-trimethylbenzoyl)-(2,4-dipentoxyphenyl)phosphine oxide, trisacylphosphine oxides, halomethyltriazines, for example 2-[2-(4-methoxy-phenyl)-vinyl]-4,6-bis-trichloromethyl-[1,3,5]triazine, 2-(4-methoxy-phenyl)-4,6-bis-trichloromethyl-[1,3,5]triazine, 2-(3,4-dimethoxy-phenyl)-4,6-bis-trichloromethyl-[1,3,5]triazine, 2-methyl-4,6-bis-trichloromethyl-[1,3,5]triazine, hexaarylbisimidazole/co-initiator systems, for example ortho-chlorohexaphenyl-bisimidazole together with 2-mercaptobenzothiazole, ferrocenium compounds or titanocenes, for example dicyclopentadienyl-bis(2,6-difluoro-3-pyrrolophenyl) titanium or borate photoinitiators.

When the photoinitiators according to the invention are used in hybrid systems, that is to say in systems that are both free-radically and cationically curable, in addition to the free-radical hardeners of formula I and optionally further free-radical hardeners there are used cationic photoinitiators, for example benzoyl peroxide (other suitable peroxides are described in U.S. Pat. No. 4,950,581, column 19, lines 17–25), aromatic sulfonium, phosphonium or iodonium salts, as described, for example, in U.S. Pat. No. 4,950,581, column 18, line 60 to column 19, line 10.

The photopolymerisable compositions contain the photoinitiator advantageously in an amount of from 0.05 to 15% by weight, preferably from 0.1 to 5% by weight, based on the composition. The amount of photoinitiator indicated relates to the sum of all the photoinitiators added when mixtures thereof are used, that is to say either to the photoinitiator (B) or to the photoinitiators (B)+(E).

The photopolymerisable compositions may be used for a variety of purposes, for example as printing inks, as clear lacquer, as white surface-coating compositions, as colour-pigmented surface-coating compositions, for example for wood or metal, as powder coating compositions, as paint, inter alia, for paper, wood, metal or plastics, as daylight-curable paint for marking structures and roads, for photographic reproduction processes, for holographic recording materials, for image recording processes or for the production of printing plates that are to be developed with organic solvents or using aqueous/alkaline media, in the production of masks for screen-printing, as dental filling compounds, as adhesives, as pressure-sensitive adhesives, as laminating resins, as etch resists or permanent resists, liquid films and dry films, as photostructurable dielectrics, and as solder masks for electronic circuits, as resists in the manufacture of colour filters for any type of screen or for producing structures in the manufacturing process of plasma displays and electroluminescent displays, in the manufacture of optical switches, optical gratings (interference gratings), in the manufacture of three-dimensional articles by means of bulk curing (UV-curing in transparent moulds) or using the stereolithography process, as described, for example, in U.S. Pat. No. 4,575,330, in the manufacture of composites (e.g. styrene polyesters that may optionally include glass fibres and/or other fibres and other adjuvants) and other thick-layered compositions, in the coating or sealing of electronic components or as coatings for optical fibres. The compositions are also suitable for the manufacture of optical lenses, for example contact lenses or Fresnel lenses, and also in the manufacture of medical apparatus, aids or implants.

The compositions can also be used in the manufacture of gels having thermotropic properties, as described, for example, in DE 19700064 and EP 678 534.

The compounds of formula I can also be used as initiators for emulsion, bead or suspension polymerisations or as initiators of a polymerisation for fixing the orientation states of liquid crystalline monomers and oligomers, and as initiators for fixing dyes on organic materials.

The photocurable compositions according to the invention are suitable, for example, as coating materials for all kinds of substrates, for example wood, textiles, paper, ceramics, glass, plastics, such as polyesters, polyethylene terephthalate, polyolefins or cellulose acetate, especially in the form of films, and metals such as Al, Cu, Ni, Fe, Zn, Mg or Co and GaAs, Si or $SiO_2$, to which a protective layer is to be applied or an image is to be applied by image-wise exposure.

The coating of the substrates can be effected by applying a liquid composition, a solution or suspension to the substrate. The choice of solvent and the concentration are governed chiefly by the nature of the composition and by the coating method. The solvent should be inert, that is to say it should not enter into any chemical reaction with the components and it should be capable of being removed again upon drying after the coating operation. Examples of suitable solvents are ketones, ethers and esters, such as methyl ethyl ketone, isobutyl methyl ketone, cyclopentanone, cyclohexanone, N-methylpyrrolidone, dioxane, tetrahydrofuran, 2-methoxyethanol, 2-ethoxyethanol, 1-methoxy-2-propanol, 1,2-dimethoxyethane, ethyl acetate, n-butyl acetate and ethyl 3-ethoxy-propionate.

The formulation is applied uniformly to a substrate by known coating methods, for example by spin-coating, immersion, knife coating, curtain pouring, brush application or spraying, especially by electrostatic spraying and reverse-roll coating, and by electrophoretic deposition. It is also possible to apply the photosensitive layer to a temporary flexible support and then coat the final substrate by transferring the layer by lamination.

The amount applied (layer thickness) and the type of substrate (layer support) are dependent upon the desired field of use. The dry layer thickness range generally includes values from about 0.1 µm to more than 100 µm, preferably from 0.02 to 2 cm.

A further field of use for photocuring is in metal coating, for example in the surface-coating of metal sheets and tubes, cans or bottle closures, and photocuring on plastics coatings, for example of PVC-based floor or wall coverings.

Examples of photocuring of paper coatings are the application of a colourless surface-coating to labels, record sleeves or book covers.

The photosensitivity of the compositions according to the invention generally ranges from about 200 nm to about 600 nm (UV field). Suitable radiation is present, for example, in sun-light or light from artificial light sources. Accordingly, a large number of widely varying types of light sources may be used. Point sources and also platform radiators (lamp carpets) are suitable. Examples thereof include: carbon arc lamps, xenon arc lamps, medium-, high- and low-pressure mercury arc lamps, doped where appropriate with metal halides (metal halide lamps), microwave-excited metal vapour lamps, excimer lamps, superactinic fluorescent tubes, fluorescent lamps, argon incandescent lamps, flashlamps, photographic flood lights, light-emitting diodes (LED), electron beams and X-rays. The distance between the lamp and the substrate to be irradiated can vary according to the intended use and upon the type and strength of the lamp, and may be, for example, from 2 cm to 150 cm. Laser light sources, for example excimer lasers, such as Krypton F lasers for irradiation at 248 nm, are especially suitable. Lasers in the visible range can also be used.

As already mentioned, in the process according to the invention curing can be effected solely by irradiation with electromagnetic radiation, but, depending upon the composition of the formulation to be cured, thermal curing before, during or after the irradiation is advantageous. The thermal curing is carried out according to methods known to the person skilled in the art. Curing is generally carried out in an oven, for example a circulating-air oven, on a hotplate or by irradiation with IR lamps. Curing at room temperature without aids is also possible, depending upon the binder system used. The curing temperatures are generally from room temperature to 150° C., for example from 25° C. to 150° C. or from 50° C. to 150° C. In the case of powder coating compositions or "coil coat" surface-coatings, the curing temperatures may even be higher, for example up to 350° C.

According to the invention, when the formulation comprises thermally curable components (C) it is also possible to add thermal drying or curing catalysts as additional additives (D) to the formulation. Examples of possible drying catalysts, or thermal curing catalysts, are organic metal compounds, amines and/or phosphines. Organic metal compounds are, for example, metal carboxylates, especially those of the metals Pb, Mn, Co, Zn, Zr or Cu, or metal chelates, especially those of the metals Al, Ti or Zr, or organometal compounds, for example organotin compounds. Examples of metal carboxylates are the stearates of Pb, Mn or Zn, the octoates of Co, Zn or Cu, the naphthenates of Mn and Co or the corresponding linoleates or tallates. Examples of metal chelates are the aluminium, titanium or zirconium chelates of acetylacetone, ethyl acetylacetate, salicylaldehyde, salicylaldoxime, o-hydroxyacetophenone or ethyl trifluoroacetylacetate and the alkoxides of those metals. Examples of organotin compounds are dibutyltin oxide, dibutyltin dilaurate and dibutyltin dioctoate. Examples of amines are especially tertiary amines, for example tributylamine, triethanolamine, N-methyldiethanolamine, N-dimethylethanolamine, N-ethylmorpholine, N-methylmorpholine or diazabicyclooctane (triethylenediamine) and salts thereof. Further examples are quaternary ammonium salts, for example trimethylbenzylammonium chloride. Phosphines, for example triphenylphosphine, can also be used as curing catalyst. Suitable catalysts are also described, for example, in J. Bielemann, Lackadditive, Wiley-VCH Verlag GmbH, Weinheim, 1998, pages 244–247. Examples thereof are carboxylic acids, such as p-toluenesulfonic acid, dodecylbenzenesulfonic acid, dinonylnaphthalenesulfonic acid and dinonylnaphthalenedisulfonic acid. Latent or blocked sulfonic acids may, for example, also be used, it being possible for the blocking of the acid to be ionic or non-ionic.

Such catalysts are used in concentrations customary in the art and known to the person skilled in the art.

The invention relates also to a process for the photopolymerisation of non-volatile monomeric, oligomeric or polymeric compounds having at least one ethylenically unsaturated double bond, in which process a composition as described above is irradiated with electromagnetic radiation in the range of from 200 nm to 600 nm.

The invention relates also to the use of the above-described composition and to a process for the preparation of pigmented and non-pigmented surface-coatings, powder coating compositions, composites and glass fibre cable coatings.

The invention relates also to a coated substrate that is coated on at least one surface with a composition as described above.

The following Examples illustrate the invention further, but it is not intended to limit the invention to the Examples. As in the remainder of the description and in the claims, unless other-wise indicated, parts and percentages relate to weight. Where mention is made of alkyl radicals having more than three carbon atoms without reference to the isomer, it is always the n-isomers that are intended.

EXAMPLE A

Preparation of the Photoinitiator Unit

A.1: Preparation of phenyl isobutyrate

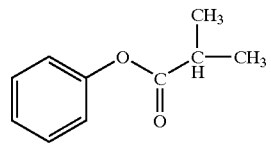

In a flask equipped with a thermometer, cooling device and dropping funnel, 176.6 g of phenol are cooled to 5° C. under nitrogen. Over the course of 40 minutes, 250 g of iso-butylic acid chloride are added dropwise, and the solution is stirred at 5° C. for one hour. The temperature is increased to room temperature and stirring is continued for 2 hours. The mixture is distilled (bp=95–100° C. (20 mbar)) and 298 g of the pure product are obtained (97%). $^1$H-NMR (CDCl$_3$) [ppm]: 7.39 (m, 2 H arom.); 7.22 (m, 1 H arom.); 7.10 (m, 2 H arom.); 3.54 (q×q, J=6.99, 1 H); 1.33(d, J=7.00, 6 H, 2 CH$_3$).

A.2: Preparation of 1-(4-hydroxyphenyl)-2-methyl-1-propanone

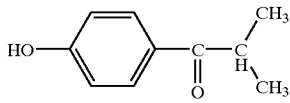

In a flask equipped with a thermometer, cooling device and dropping funnel, 580.8 g of aluminium chloride are added to 1 liter of chlorobenzene at 0–5° C. under nitrogen. The mixture is stirred at room temperature for 45 minutes. 298 g of the product prepared as described in A.1 are added dropwise over the course of 45 minutes, the temperature being maintained at 20–25° C. The resulting suspension is stirred at room temperature for 2 days. The mixture is poured into a mixture of ice (3 kg) and hydrochloric acid (450 ml) and extracted with toluene. The organic phases are washed with salt water. After drying over $MgSO_4$ and filtration, the solvent is removed in vacuo. 1 liter of water is added to the residue, and the pH value of the solution is raised to 14 with 30% sodium hydroxide solution, whilst maintaining the temperature at 20° C. The solution is extracted with ethyl acetate. The aqueous phase is cooled to 0° C. and the pH value is adjusted to 0 with concentrated hydrochloric acid, the organic phase is dried over $MgSO_4$ and filtered and the solvent is removed in vacuo, resulting in a liquid which solidifies in a freezer. The pure product is obtained in the form of a white solid (213 g, 71%).

$^1$H-NMR (CDCl$_3$) [ppm]: 7.90 (m, 2 H arom.); 6.94 (m, 2 H arom.); 3.54 (q×q, J=6.84, 1 H); 1.20 (d, J=6.82, 6 H, 2 CH$_3$).

A.3: Preparation of 2-hydroxy-1-(4-hydroxyphenyl)-2-methyl-1-propanone

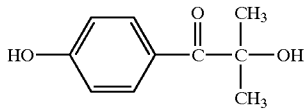

A solution of 213 g of the product prepared in A.2 in 475 ml of dioxane is cooled to 0° C. 228 g of bromine are added dropwise over the course of one hour, whilst maintaining the temperature at 10–15° C. The orange-coloured mixture is stirred at room temperature for 2 hours. The solution is poured into water (5.4 liters) and extracted with ethyl acetate. After drying the organic phases over $MgSO_4$ and filtering, the solvent is removed in vacuo, resulting in a brown oil. 3 liters of water are added to the oil, and the beige-coloured emulsion that forms is treated with 650 g of 30% sodium hydroxide solution. The mixture is stirred at room temperature for 3 hours. 293 ml of concentrated HCl are then added to adjust the pH value of the solution to 7. The resulting white suspension is stirred at 0° C. for 4 hours and at room temperature overnight. The mixture is then cooled to 5° C. and filtered. The crystals are washed with water and dried in vacuo at 40° C. Initially 137.8 g are obtained in the form of dirty-white crystals. A further 47.8 g of a contaminated compound are obtained from the extracted mother liquor. Both products are purified in toluene and 135 g (58%) of pure product and 27 g (12%) of a product that is not quite pure are isolated.

$^1$H-NMR (DMSOd$_6$) [ppm]: 10.23 (s, OH); 8.12 (m, 2 H arom.); 6.79 (m, 2 H arom.); 5.59 (s, OH); 1.37 (s, 6 H, 2 CH$_3$). Microanalysis: calc.: C, 66.65; H, 6.71; found: C, 65.60; H, 6.52.

A.4: Preparation of 2-hydroxy-2-methyl-1-[4-(2-propenyloxy)phenyl]-1-propanone (A4a) and 2-methyl-2-(2-propenyloxy)-1-[4-(2-propenyloxy)phenyl]-1-propanone (A4b)

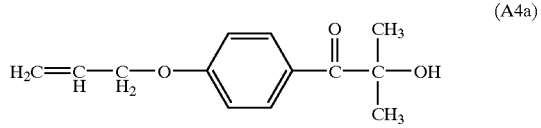
(A4a)

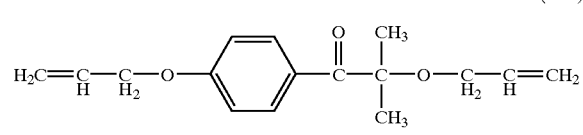
(A4b)

A solution of 75 g of the compound prepared as described in A.3 in 300 ml of dimethyl sulfoxide (DMSO) is added over the course of one hour, at room temperature under argon, to a suspension of NaH (20 g; 55–60% in oil) in 950 ml of DMSO. The solution is stirred for 15 minutes at room temperature and for a further 15 minutes at 35–40° C. A solution of 38.7 ml of allyl bromide in 75 ml of DMSO is added over the course of 15 minutes and the resulting mixture is heated at 45° C. for 30 minutes. The orange-coloured mixture is poured into an ice/water mixture (2.5 liters) and extracted with tert-butyl methyl ether. The organic phases are washed with water and dried over magnesium sulphate. Filtration, removal of the solvent by evaporation and chromatography (eluant hexane/ethyl acetate 5:1 to 4:1) yield 2-hydroxy-2-methyl-1-[4-(2-propenyloxy)phenyl]-1-propanone (53 g, 58%) in the form of a slightly yellowish solid and 2-methyl-2-(2-propenyloxy)-1-[4-(2-propenyloxy)phenyl]-1-propanone (17.6 g; 16%) in the form of an oil.

A4a: 2-Hydroxy-2-methyl-1-[4-(2-propenyloxy)phenyl]-1-propanone

U.V. (CH$_3$CN) max. at 273 nm (e 16 482). IR (KBr film, cm$^{-1}$): 3452 (OH); 1663 (CO). $^1$H-NMR (CDCl$_3$) [ppm]: 8.02 (m, 2 H arom.); 6.92 (m, 2 H arom.); 6.01 (m, 1 H, allyl); 5.37 (m, 2 H, allyl); 4.60 (m, 2 H, CH$_2$—O); 4.28 (s, OH); 1.62 (s, 6 H, 2 CH$_3$). $^{13}$C-NMR (CDCl$_3$) [ppm]: 162.5 (C$_{arom}$—O); 132.5 (CH allyl); 132.4 (arom.); 118.3 (CH$_2$ allyl); 114.4 (arom.); 75.8 (C(CH$_3$)$_2$OH); 69.0 (CH$_2$—O—Ph); 28.8 (CH$_3$). Microanalysis: calc.: C, 70.89; H, 7.32; found: C, 70.86; H, 7.42

A4b: 2-Methyl-2-(2-propenyloxy)-1-[4-(2-propenyloxy)phenyl]-1-propanone

U.V. (CH$_3$CN) max. at 275 nm (e 16 467). $^1$H-NMR (CDCl$_3$) [ppm]: 8.30 (m, 2 H arom.); 6.92 (m, 2 H arom.); 6.05 (m, 1 H, allyl); 5.80 (m, 1 H, allyl); 5.45–5.08 (m, 4 H, allyl); 4.60 (m, 2 H, CH$_2$—O); 3.82 (m, 2 H, CH$_2$—O); 1.54 (s, 6 H, 2 CH$_3$).

EXAMPLE B

Preparation of a Catalyst

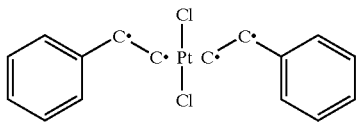

A mixture of 20 ml of freshly distilled styrene and 1 g of platinum(II) chloride is stirred at room temperature for 40 hours. The orange-coloured suspension is filtered and the resulting solid is washed with toluene and hexane.

$^1$H-NMR (DMSO-$d_6$): 7.35 (m, 5 H arom.); 6.72 (dd, J=10.9, J=17.6, 1 H, Ph—CH); 5.81 (d, J=17.6, 1 H); 5.25 (d, J=10.8, 1 H). Microanalysis: calc: C 40.52; H 3.40; found: C 40.45; H 3.03.

Example 1

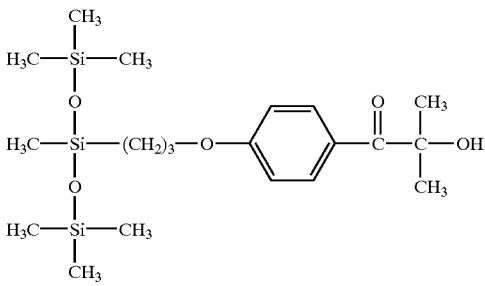

(n=1, m=p=0, x=1, $R_1$, $R_5$, $R_6$, $R_7$, $R_8$, $R_9$, $R_{10}$, $R_{13}$, $R_{14}$=$CH_3$, Y=—($CH_2$)$_3$—O—, X=OH)

A mixture of one equivalent of 2-hydroxy-2-methyl-1-[4-(2-propenyloxy)phenyl]-1-propanone and one equivalent of 1,1,1,3,5,5,5-heptamethyltrisiloxane in toluene is heated at 90° C. for 18 hours in the presence of 0.012 equivalent (120 ppm, based on the Pt content) of a Pt catalyst supported by aluminium oxide. The mixture is then filtered and the resulting solution is treated with activated carbon. Filtration and removal of the solvent by evaporation yield the compound quantitatively in the form of an oil.

U.V. ($CH_3CN$) max. at 274 nm ($\epsilon$16 299). $^1$H-NMR (CDCl$_3$) δ [ppm]: 8.02 (m, 2 H, ArH); 6.94 (m, 2 H, ArH); 4.30 (s, OH); 3.99 (m, 2 H, Ph—OCH$_2$); 1.83 (m, 2 H, Ph—OCH$_2$—C$\underline{H}_2$); 1.59 (s, 6 H, 2 CH$_3$); 0.58 (m, 2 H, CH$_2$—Si); 0.05 (s, 21 H, 7 Si—CH$_3$). m/z (EI) 427 (M$^+$-15); according to the mass spectrum, small amounts of further compounds are also present: 647 (M$^+$-15); 605 (M$^+$-15); 385 (M$^+$-15); 220 (M$^+$); 180 (M$^+$). Title product M=442

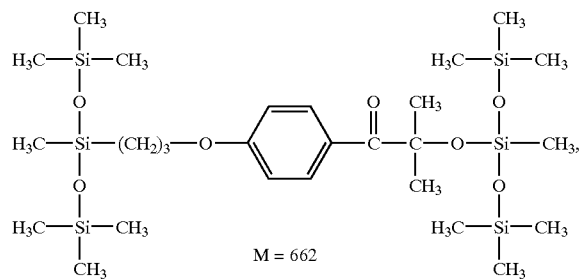

M = 662

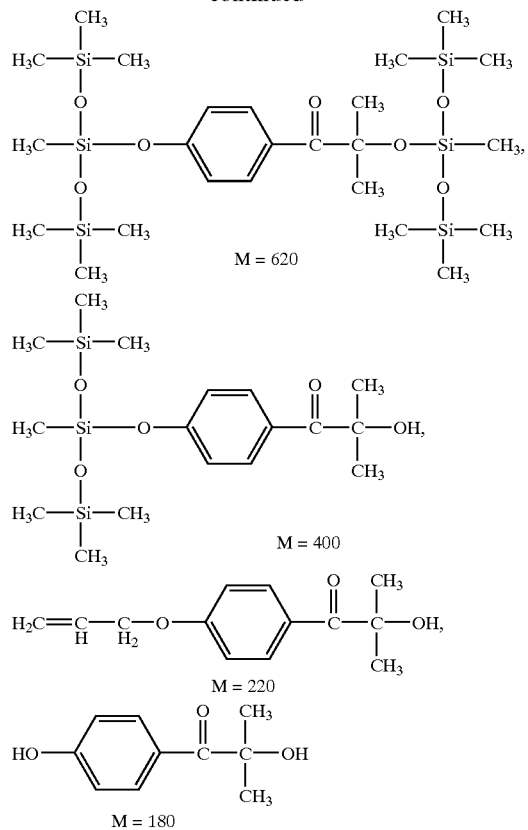

A sample is purified by flash chromatography and a product of M=442 and 85% purity (determined by gas chromatography) is obtained. Impurity remains as a result of the product of M=400.

U.V. (CH$_3$CN) max. at 274 nm ($\epsilon$16 761).

Example 2

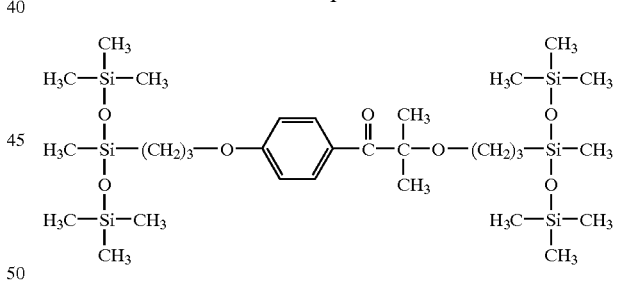

(x=2; n=1; m, p=0; $R_1$, $R_5$, $R_6$, $R_7$, $R_8$, $R_9$, $R_{10}$, $R_{13}$, $R_{14}$=CH$_3$; Y, $X_1$=—(CH$_2$)$_3$—O—)

The compound of Example 2 is prepared according to the method described in Example 1, using 1 molar equivalent of 2-methyl-2-(2-propenyloxy)-1-[4-(2-propenyloxy)phenyl]-1-propanone and 2 molar equivalents of 1,1,1,3,5,5,5-heptamethyltrisiloxane.

U.V. (CH$_3$CN) max. at 275 nm ($\epsilon$14 666). $^1$H-NMR (CDCl$_3$) δ [ppm]: 8.30 (m, 2 H, arom.); 6.87 (m, 2 H, arom.); 3.98 (m, 2 H, Ph—OCH$_2$); 3.23 (m, 2 H, Ph—C(O)—C(CH$_3$)$_2$—OC$\underline{H}_2$); 1.80 (m, 2 H, Ph—OCH$_2$—C$\underline{H}_2$); 1.54 (m, 2 H, Ph—C(O)—C(CH$_3$)$_2$—O—CH$_2$C$\underline{H}_2$); 1.50 (s, 6 H, 2 CH$_3$); 0.60 (m, 2 H, CH$_2$—Si); 0.34 (m, 2 H, CH$_2$—Si); 0.10 (m, 42 H, 14 Si—CH$_3$). m/z (CI): 705 (MH$^+$); according to the mass spectrum, small amounts of further compounds are also present: 663 (MH$^+$); 621 (MH$^+$); 443 (MH$^+$); 401 (MH$^+$); 459 (MH$^+$); 265 (MH$^+$); 239 (MH$^+$). M=662, M=620, M=442, M=400 cf. the structures shown in Example 1. The values MH+=459, 265 and 239 are to be assigned to different siloxane chains.

Example 3

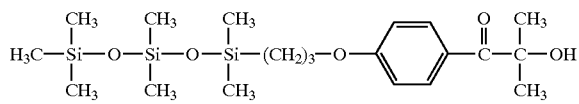

(x, n, p=1; m=0; $R_1$, $A_1$, $R_3$, $R_4$, $R_8$, $R_9$, $R_{10}$, $R_{13}$, $R_{14}$=$CH_3$; Y=—$(CH_2)_3$—O—; X=OH)

The compound of Example 3 is obtained according to the method described in Example 1, reacting 1 molar equivalent of 2-hydroxy-2-methyl-1-[4-(2-propenyloxy)phenyl]-1-propanone and 1 molar equivalent of 1,1,3,3,5,5,5-heptamethyltrisiloxane.

U.V. ($CH_3CN$) max. at 274 nm ($\epsilon$24 989). $^1$H-NMR (CDCl$_3$) δ [ppm]: 7.94 (m, 2 H arom.); 6.81 (m, 2 H arom.); 4.34 (OH); 3.91 (m, 2 H, Ph—OCH$_2$); 1.80 (m, 2 H, Ph—OCH$_2$—CH$_2$); 1.55 (s, 6 H, 2 CH$_3$); 0.57 (m, 2 H, CH$_2$—Si); 0.01 (m, 21 H, 7 Si—CH$_3$). m/z (EI) (% ratio determined by GC-MS): 663 (MH+)(18%); 443 (MH+)(57%); 441 (MH+)(3%); 401 (MH+)(3%); 221 (MH+)(8); 181 (MH+)(8%).

Title product M=442

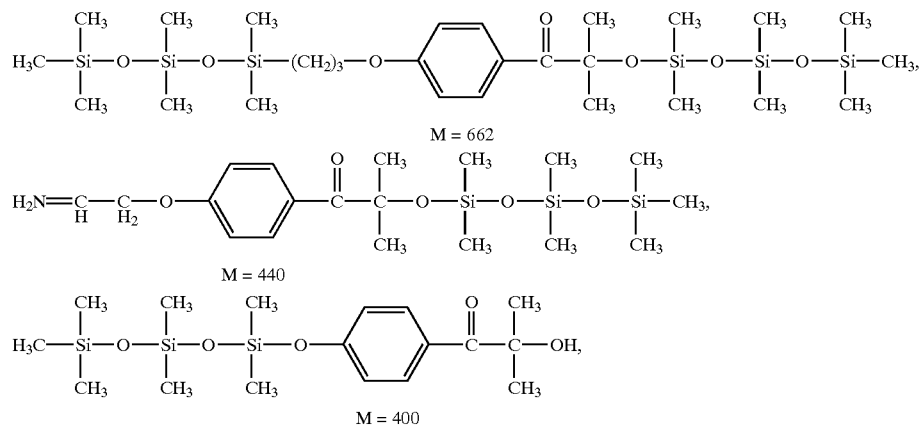

M=220 and M=180 cf. Examples 1.

A sample is purified by flash chromatography and the pure product of M=442 is isolated. U.V. (CH$_3$CN) max. at 274 nm ($\epsilon$27 180).

Example 4

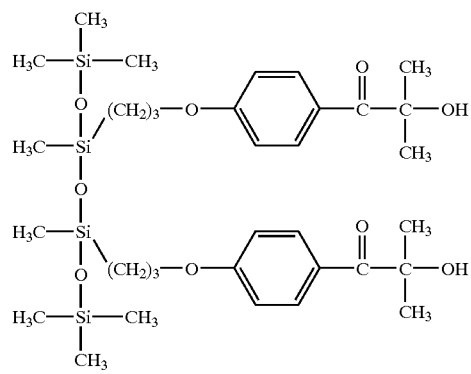

(n=2; x=1; m, p=0; $R_1$, $R_5$, $R_6$, $R_7$, $R_8$, $R_9$, $R_{10}$, $R_{13}$, $R_{14}$=$CH_3$; Y=—$(CH_2)_3$—O—; X=OH)

A mixture of 2 molar equivalents of 2-hydroxy-2-methyl-1-[4-(2-propenyloxy)phenyl]-1-propanone and 1 molar equivalent of 1,1,1,3,5,7,7,7-octamethyltetrasiloxane in 50 ml of toluene is heated for 18 hours at 60° C. in the presence of 0.01 equivalent of a styrene/platinum dichloride complex (prepared as described in Example B). A further 0.1 equivalent of the catalyst is added, and the mixture is heated again for 22 hours. Filtration is then carried out over diatomaceous earth ("Celite"). Removal of the solvent by evaporation yields a brown oil, which is taken up in ethyl acetate and treated with activated carbon. Filtration and removal of the solvent by evaporation yield the desired product in a quantitative yield in the form of a yellow oil.

U.V. (CH$_3$CN) max. at 274 ($\epsilon$22 657). $^1$H-NMR (CDCl$_3$) δ [ppm]: 7.91 (m, 4 H arom.); 6.83 (m, 4 H arom.); 4.21–3.85 (m, 4 H, 2 Ph—OCH$_2$); 1.76 (m, 4 H, 2 Ph—OCH$_2$—CH$_2$); 1.52 (br. s, 12 H, 4 CH$_3$); 0.95 (m, 2 H, CH$_2$—Si); 0.55 (m, 2 H, CH$_2$—Si); 0.01 (m, 24 H, 8 Si—CH$_3$). m/z (EI): 707 (M+–15); 221 (MH+). Title product: M=722; M=220 cf. Example 1.

Example 5

(n=2; p, x=1; m=0; $R_1$, $R_3$, $R_4$, $A_1$, $A_2$, $R_{13}$, $R_{14}$=$CH_3$; Y=—$(CH_2)_3$—O—; X=OH)

The compound of Example 5 is obtained according to the method described in Example 1, using 2 molar equivalents of 2-hydroxy-2-methyl-1-[4-(2-propenyloxy)phenyl]-1-propanone and 1 molar equivalent of 1,1,3,3,5,5-hexamethyltrisiloxane.

U.V. (CH₃CN) max. at 274 (ε25 286). ¹H-NMR (CDCl₃), δ [ppm]: 7.97 (m, 4 H arom.); 6.78 (m, 4 H arom.); 4.20 (OH), 3.95 (m, 4 H, 2 Ph—OCH₂); 1.73 (m, 4 H, Ph—OCH₂—C$\underline{H}$₂); 1.49 (s, 12 H, 4 CH₃); 0.48 (m, 4 H, 2 CH₂—Si); 0.01 (m, 18 H, 6 Si—CH₃). m/z (Cl): 631 (M⁺–18); 613 (M⁺–(2×18)); 221 (MH⁺).

Example 6

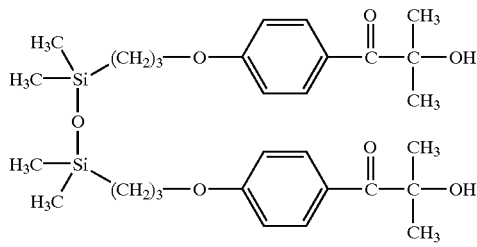

(n=2; x=1; m, p=0; R₁, A₁, A₂, R₁₃, R₁₄=CH₃; Y= —(CH₂)₃—O—; X=OH)

The compound of Example 6 is prepared according to the method described in Example 1, using 2 molar equivalents of 2-hydroxy-2-methyl-1-[4-(2-propenyloxy)phenyl]-1-propanone and 1 molar equivalent of 1,1,3,3-tetramethyldisiloxane. According to the ¹H-NMR spectrum, approximately 50% of the 2-hydroxy-2-methyl-1-[4-(2-propenyloxy)phenyl]-1-propanone (starting material, "sm") remain unreacted.

U.V. (CH₃CN) max. at 274 (ε32 443). ¹H-NMR (CDCl₃) δ [ppm]: 8.19 (m, 2 H arom. sm); 7.97 (m, 4 H arom.); 6.78 (m, 4 H arom.); 5.99 (m, 1 H allyl sm); 5.31 (m, 2 H allyl sm); 4.41 (m, 2 H allyl sm); 4.20 (br. s, OH); 3.95 (m, 4 H, 2 Ph—OCH₂); 1.80 (m, 4 H, 2 Ph—OCH₂—C$\underline{H}$₂); 1.56 (s, 12 H, 4 CH₃); 0.56 (m, 4 H, 2 CH₂—Si); 0.01 (m, 12 H, 4 Si—CH₃). m/z (Cl): 707 (MH⁺); 575 (MH⁺); 533 (MH⁺); 491 (MH⁺); 221 (MH⁺); 181 (MH³⁰). Title product: M=574

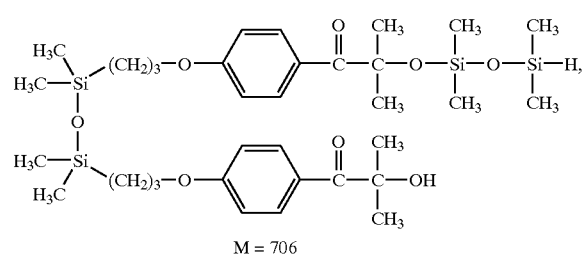

M = 706

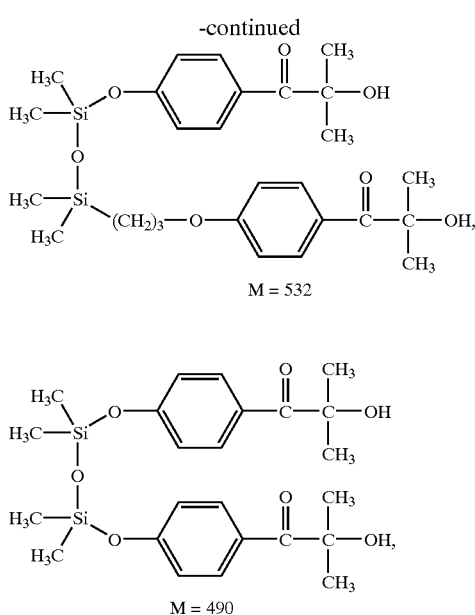

M = 532

M = 490

M=220 and M=180 cf. Example 1.

Example 7

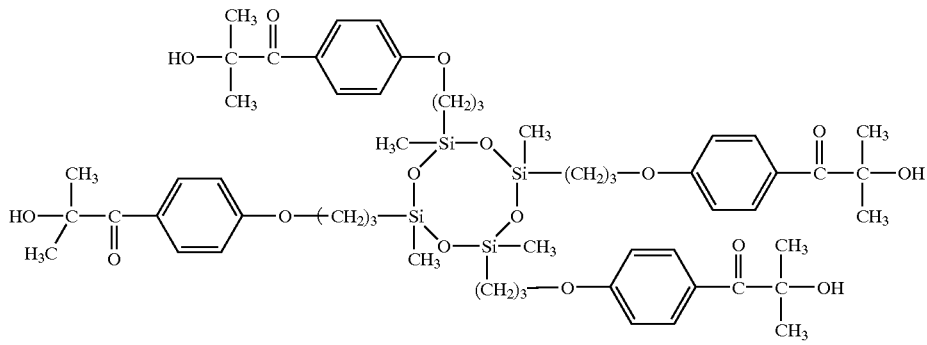

(n=4; x=1; m, p=0; A₁+A₂=single bond; R₁, R₁₃, R₁₄=CH₃; Y=—(CH₂)₃—O—; X=OH)

The compound of Example 7 is prepared according to the method described in Example 1, using 4 molar equivalents of 2-hydroxy-2-methyl-1-[4-(2-propenyloxy)phenyl]-1-propanone and 1 molar equivalent of 2,4,6,8-tetramethylcyclotetrasiloxane. According to the ¹H-NMR spectrum, after the reaction the mixture still contains approximately 36% 2-hydroxy-2-methyl-1-[4-(2-propenyloxy)phenyl]-1-propanone (starting material, "sm").

U.V. (CH₃CN) max. at 274 (ε58 856). ¹H-NMR (CDCl₃) δ [ppm]: 7.90 (m, 8 H arom.); 6.77 (m, 8 H arom.); 5.9 (m, 1 H allyl sm); 5.25 (m, 2 H allyl sm); 4.41 (m, 2 H allyl sm); 4.10 (m OH); 3.90 (m, 8 H, 4 Ph—OCH₂); 1.71 (m, 8 H, 4 Ph—OCH₂—C$\underline{H}$₂); 1.47 (s, 24 H, 8 CH₃); 0.54 (m, 8 H, 4 CH₂—Si); 0.01 (m, 12 H, 4 Si—CH₃). ¹³C-NMR (CDCl₃) δ [ppm]202.5 (CO);162.9, 162.5, 160.8 (C$_{arom}$—O); 132.3–114.0 (arom.); 75.9 ($\underline{C}$(CH₃)₂OH); 70.2 (CH₂—O—O—Ph); 28.6 (CH₃); 22.7 ($\underline{C}$H₂—CH₂—O—Ph); 13.0 (CH₂—Si); –0.7 (CH₃—Si); m/z (Cl): 1121 (MH⁺); 943 (MH⁺); 901 (MH⁺); m/z 221 (MH⁺);

Title product: M=1120

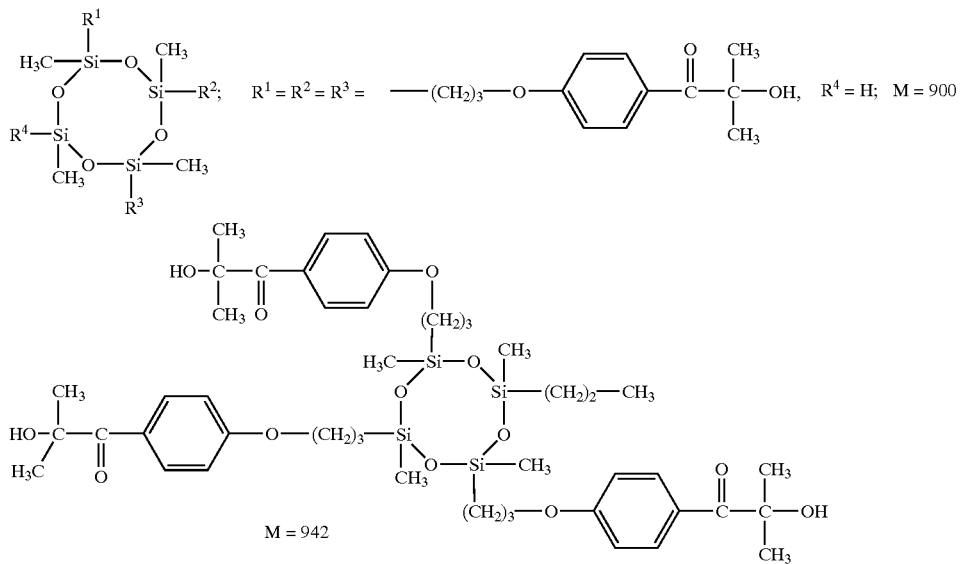

Example 8

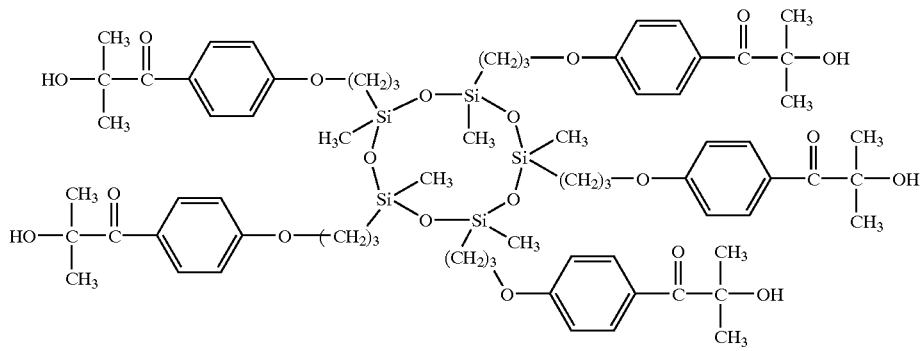

(n=5; x=1; m, p=0; $A_1+A_2$=single bond; $R_1$, $R_{13}$, $R_{14}$=$CH_3$; Y=—$(CH_2)_3$—O—; X=OH)

The compound of Example 8 is obtained according to the method described in Example 1, using 5 molar equivalents of 2-hydroxy-2-methyl-1-[4-(2-propenyloxy)phenyl]-1-propanone and 1 molar equivalent of 2,4,6,8,10-pentamethylcyclopentasiloxane.

U.V. ($CH_3CN$) max. at 275 ($\epsilon$61 882). $^1$H-NMR ($CDCl_3$) $\delta$ [ppm]: 7.87 (m, 10 H arom.); 6.72 (m, 10 H arom.); 4.10 (m, OH); 3.7 (m, 10 H, 5 Ph—$OCH_2$); 1.7–0.8 (m, 40 H, 5 Ph—$OCH_2$—$\underline{CH}_2$ and 10 $CH_3$); 0.5 (m, 10 H, 5 $CH_2$—Si); 0.01 (m, 15 H, 5 Si—$CH_3$). m/z (Cl): 1401 ($MH^+$); 1181 ($MH^+$); 960 ($MH^+$); 221 ($MH^+$).

Title compound M=1400

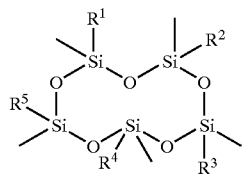

-continued

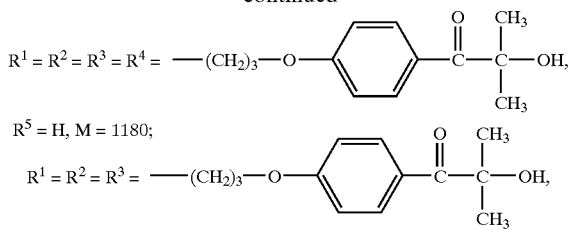

$R^4=R^5=H$, M=960; M=220, cf. Example 1.

Example 9

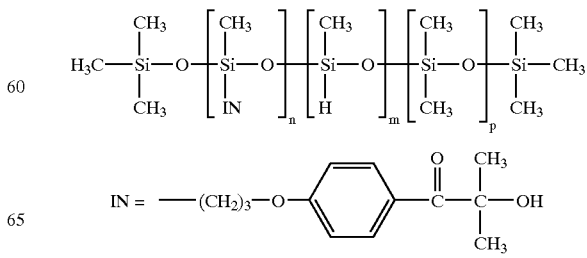

(n≅0.8; m≅0.4; p≅23.75; x=1; $R_1, R_2, R_3, R_4, R_5, R_6, R_7, R_8, R_9, R_{10}, R_{13}, R_{14}$=$CH_3$; Y=—$(CH_2)_3$—O—; X=OH)

The compound of Example 9 is obtained according to the method described in Example 1, using 29 molar equivalents of 2-hydroxy-2-methyl-1-[4-(2-propenyloxy)phenyl]-1-propanone and 1 molar equivalent of methylhydrosiloxane/dimethylsiloxane copolymer having 6–7 mol % methylhydrosiloxane groups and a molecular weight of from 1900 to 2000 (HMS 071, Gelest, Del.).

According to the $^1$H-NMR spectrum, the product still contains approximately 33% 2-hydroxy-2-methyl-1-[4-(2-propenyloxy)phenyl]-1-propanone (starting material "sm"). The $^1$H-NMR spectrum also shows that the content of methylhydrosiloxane groups is 5%, of which 67% have been substituted by a photoinitiator group (IN), that is to say n=0.83, m=0.41, p=23.75.

$^1$H-NMR (CDCl$_3$) δ [ppm]: 7.94 (m, H arom.); 6.85 (m, H arom.); 5.95 (m, H allyl sm); 5.28 (m, H allyl sm); 4.52 (m, H allyl sm); 4.24 (m, OH); 3.90 (m, Ph—OCH$_2$); 1.76 (m, Ph—OCH$_2$—C$\underline{H}_2$); 1.55 (s, CH$_3$); 0.56 (m, CH$_2$—Si); 0.01 (m, Si—CH$_3$). $^{13}$C-NMR (CDCl$_3$): 202 (CO); 163 (C$_{arom}$—O); 132.3–114.0 (arom.); 70.5 ($\underline{C}$(CH$_3$)$_2$OH); 68.9 (CH$_2$—O—Ph); 28.7 (CH$_3$); 22.8 (C$\underline{H}_2$—CH$_2$—O—Ph); 13.3 (CH$_2$—Si); 1.1, 1.0, 0.8 (CH$_3$—Si).

Example 10

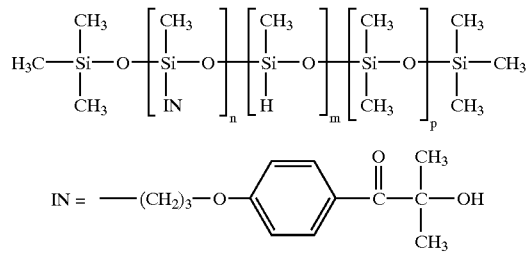

The compound of Example 10 is prepared analogously to the method described in Example 1, using 1 molar equivalent (based on the Si—H groups) of 2-hydroxy-2-methyl-1-[4-(2-propenyloxy)phenyl]-1-propanone and 1 molar equivalent of methylhydrosiloxane/dimethyl-siloxane copolymer with 1.78 mmol/g(resin) of methylhydrosiloxane groups (VXL Fluid, Witco).

$^1$H-NMR (CDCl$_3$) δ [ppm]: 7.95 (m, H arom.); 6.8 (m, H arom.); 4.25 (m, OH); 3.9 (m, Ph—OCH$_2$); 1.75 (m, Ph—OCH$_2$—C$\underline{H}_2$); 1.5 (s, CH$_3$); 0.55 (m, CH$_2$—Si); 0.01 (m, Si—CH$_3$).

Example 11

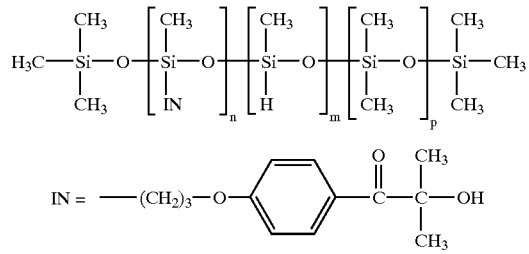

The compound of Example 11 is prepared according to the method described in Example 1, using 1 molar equivalent (based on the Si—H groups) of 2-hydroxy-2-methyl-1-[4-(2-propenyloxy)phenyl]-1-propanone and 1 molar equivalent of methylhydrosiloxane/dimethylsiloxane copolymer with 7.05 mmol/g(resin) of methylhydrosiloxane groups (Y 12183, Witco).

$^1$H-NMR (CDCl$_3$) δ [ppm]: 7.9 (m, H arom.); 6.75 (m, H arom.); 4.15 (m, OH); 3.85 (m, Ph—OCH$_2$); 1.75 (m, Ph—OCH$_2$—C$\underline{H}_2$); 1.45 (br. s, CH$_3$); 0.55 (m, CH$_2$—Si); 0.01 (m, Si—CH$_3$).

Example 12

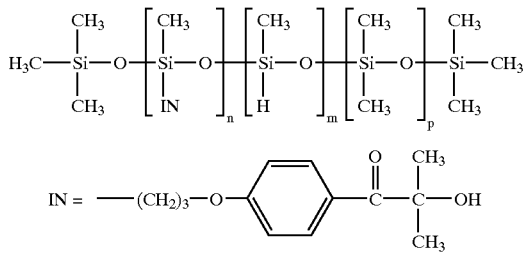

The compound of Example 12 is prepared as described in Example 1, using 1 molar equivalent (based on Si—H groups) of 2-hydroxy-2-methyl-1-[4-(2-propenyloxy)phenyl]-1-propanone and 1 molar equivalent of methylhydrosiloxane/dimethylsiloxane copolymer with 15.62 mmol/g(resin) of methylhydrosiloxane groups (Fluid L31, Witco).

According to the $^1$H-NMR spectrum, the product still contains approximately 33% 2-hydroxy-2-methyl-1-[4-(2-propenyloxy)phenyl]-1-propanone ( starting material "sm").

$^1$H-NMR (CDCl$_3$) δ [ppm]: 7.94 (m, H arom.); 6.85 (m, H arom.); 5.95 (m, H allyl sm); 5.25 (m, H allyl sm); 4.52 (m, H allyl sm); 4.22 (m, OH); 3.90 (m, Ph—OCH$_2$); 1.65 (m, Ph—OCH$_2$-C$\underline{H}_2$); 1.55 (s, CH$_3$); 0.6 (m, CH$_2$—Si); 0.01 (m, Si—CH$_3$).

Example 13

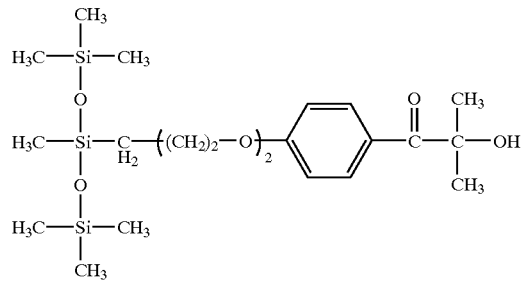

The compound of Example 13 is prepared according to the process described in Example 1, using 1 molar equivalent of 1-[4-(2-allyloxy-ethoxy)-phenyl]-2-hydroxy-2-methyl-propan-1-one and 1 molar equivalent of 1,1,1,3,5,5,5-heptamethyltrisiloxane.

U.V. (CH$_3$CN) max. at 273 nm (ϵ13 811). $^1$H-NMR (CDCl$_3$): 7.96 (m, 2 H, arom.); 6.87 (m, 2 H, arom.); 4.38 (OH); 4.09 (m, 2 H, Ph—OCH$_2$); 3.71 (m, 2 H, Ph—O (CH$_2$)$_2$—O—C$\underline{H}_2$); 3.40 (m, 2 H, Ph—OCH$_2$C$\underline{H}_2$); 1.53 (m, 2 H, Ph—O(CH$_2$)$_2$—OCH$_2$—C$\underline{H}_2$); 1.53 (s, 6 H, 2 CH$_3$); 0.38 (m, 2 H, CH$_2$—Si); 0.01 (m, 21 H, 7 Si—CH$_3$). m/z (EI and Cl) : 486 (M$^+$); according to the MS spectrum, small amounts of the following compounds are also present: 486

(M+) (second signal); 442 (M+); 264 (M+)(2 signals); 246 (M+); 238 (M+). The values M=264 (second signal) and 238 are assigned to different siloxane chains.

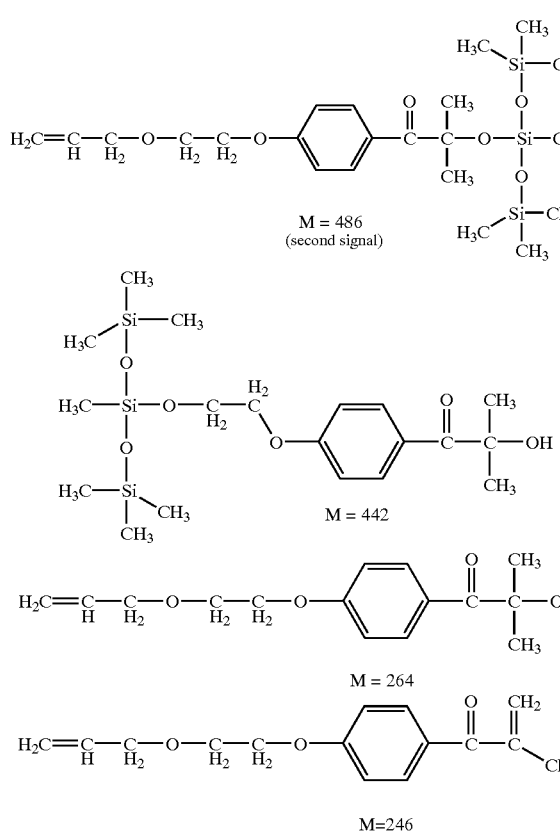

Example 14

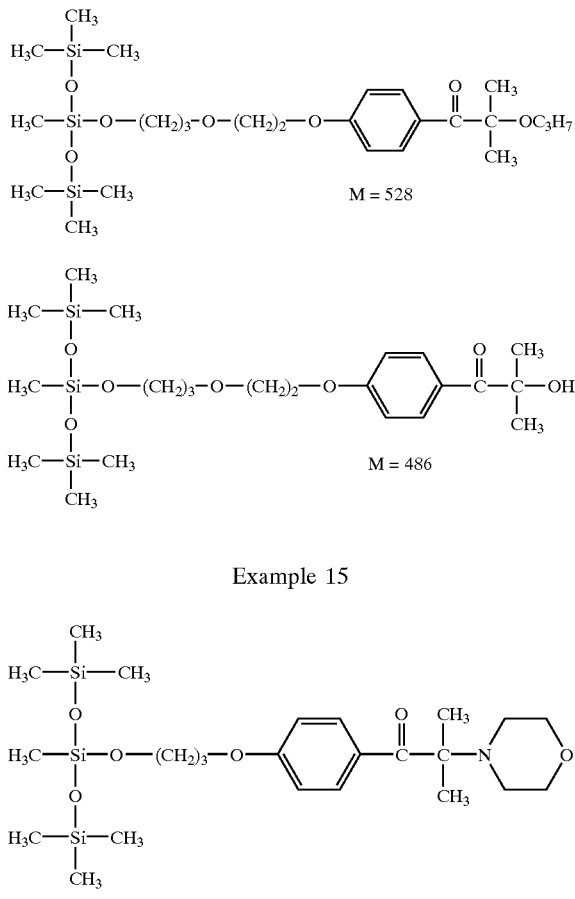

Example 15

The compound of Example 15 is prepared according to the method described in Example 1, using 1 molar equiva-

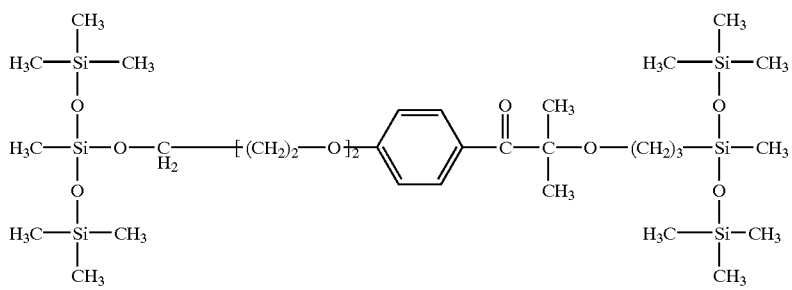

The compound of Example 14 is prepared as described in Example 1, using 1 molar equivalent of 2-allyloxy-1-[4-(2-allyloxy-ethoxy)-phenyl]-2-methyl-propan-1-one and 2 molar equivalents of 1,1,1,3,5,5,5-heptamethyltrisiloxane.

U.V. (CH$_3$CN) max. at 276 nm ($\epsilon$11 693). $^1$H-NMR (CDCl$_3$): 8.24 (m, 2 H, arom.); 5.94 (m, 2 H, arom.); 4.09 (m, 2 H, Ph—OCH$_2$); 3.71 (m, 2 H, Ph—O(CH$_2$)$_2$—O—C$\underline{H}_2$); 3.40 (m, 2 H, Ph—OCH$_2$C$\underline{H}_2$); 3.13 (m, 2 H, C(CH$_3$)$_2$—OC$\underline{H}_2$); 1.54 (m, 4 H, Ph—O(CH$_2$)$_2$—OCH$_2$—CH$_2$ and C(C$\underline{H}_3$)$_2$—OCH$_2$—C$\underline{H}_2$); 1.42 (s, 6 H, 2 CH$_3$); 0.38 (m, 4 H, 2 CH$_2$—Si); 0.01 (m, 42 H, 14 Si—CH$_3$). m/z (EI and Cl): 748 (M+); according to the MS spectrum, small amounts of compounds of 528 (M+); and 486 (M+) are also present.

lent of 1-(4-allyloxy-phenyl)-2-methyl-2-morpholin-4-yl-propan-1-one and 1 molar equivalent of 1,1,1,3,5,5,5-heptamethyltrisiloxane.

U.V. (CH$_3$CN) max. at 273 nm ($\epsilon$15 248). $^1$H-NMR (CDCl$_3$): 8.47 (m, 2 H, arom.); 6.79 (m, 2 H, arom.); 4.09 (t, 2 H, Ph—OCH$_2$, J=6); 3.58 (m, 4 H, N=(CH$_2$—C$\underline{H}_2$)$_2$=O); 2.46 (m, 4 H, N=(C$\underline{H}_2$—CH$_2$)$_2$=O); 1.73 (m, 2 H, Ph—O—CH$_2$C$\underline{H}_2$); 1.21 (s, 6 H, 2 CH$_3$); 0.49 (m, 2 H, CH$_2$—Si); 0.01 (m, 21 H, 7 Si—CH$_3$). m/z (EI and Cl): 512 (MH+); according to the MS spectrum, small amounts of compounds 512 (MH+)(second signal); 470 (MH+); and 265 (MH+) are also present. The value MH+=265 is assigned to a siloxane chain.

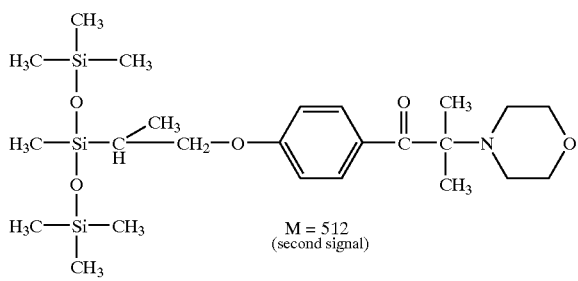

M = 512
(second signal)

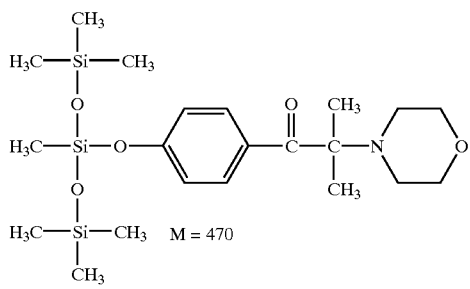

M = 470

Example 16

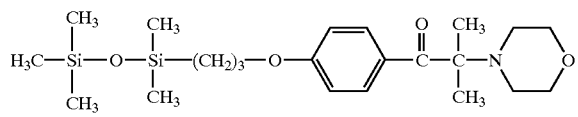

The compound of Example 16 is prepared according to the method described in Example 1, using 1 molar equivalent of 1-(4-allyloxy-phenyl)-2-methyl-2-morpholin-4-yl-propan-1-one and 1 molar equivalent of 1,1,3,3,3-pentamethyldisiloxane.

U.V. (CH$_3$CN) max. at 273 nm ($\epsilon$14 281). $^1$H-NMR (CDCl$_3$): 8.51 (m, 2 H, arom.); 6.79 (m, 2 H, arom.); 3.90 (t, 2 H, Ph—OCH$_2$, J=6); 3.60 (m, 4 H, N═(CH$_2$—CH$_2$)$_2$═O); 2.48 (m, 4 H, N═(CH$_2$—CH$_2$)$_2$═O); 1.77 (m, 2 H, Ph—O—CH$_2$CH$_2$); 1.23 (s, 6 H, 2 CH$_3$); 0.56 (m, 2 H, CH$_2$—Si); 0.01 (m, 15 H, 5 Si—CH$_3$). m/z (EI and Cl): 438 (MH$^+$) (Cl); according to the MS spectrum, small amounts of compounds 396 (MH$^+$); and 290 (MH$^+$) are also present.

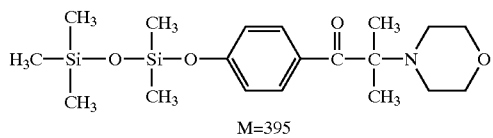

M=395

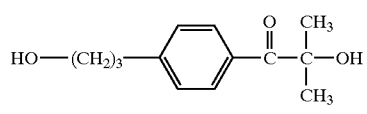

M=289

Example 17

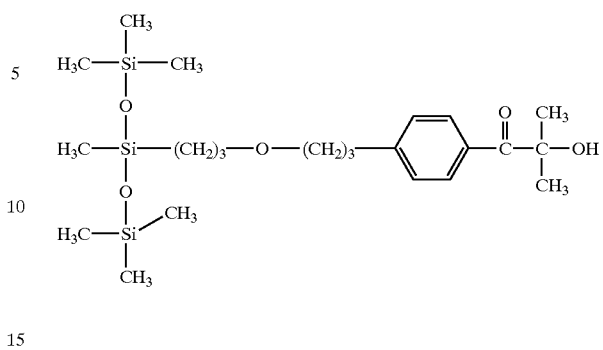

The compound of Example 17 is obtained according to the method described in Example 1, using 1 molar equivalent of 1-[4-(3-allyloxy-propyl)-phenyl]-2-hydroxy-2-methyl-propan-1-one and 1 molar equivalent of 1,1,1,3,5,5,5-heptamethyltrisiloxane.

U.V. (CH$_3$CN) max. at 255 nm ($\epsilon$13 289). $^1$H-NMR (CDCl$_3$): 7.89 (m, 2 H, arom.); 7.18 (m, 2 H, arom.); 3.30 (m, 4 H, Ph—(CH$_2$)$_2$—CH$_2$—O—CH$_2$); 2.63 (m, 2 H, Ph—CH$_2$); 1.84 (m, 2 H, Ph—(CH$_2$)$_3$—O—CH$_2$—CH$_2$); 1.54 (s, 6 H, 2 CH$_3$); 1.47 (m, 2 H, Ph—CH$_2$—CH$_2$); 0.38 (m, 2 H, CH$_2$—Si); 0.01 (m, 21 H, 7 Si—CH$_3$). m/z (EI and Cl): 484 (M$^+$); according to the mass spectrum, small amounts of 484 (M$^+$) (second isomer); 338 (M$^+$); 310 (M$^+$=338−18); 262 (M$^+$); 244 (M$^+$=262−18); 222 (M$^+$); and 204 (M$^+$=222−18) are also present.

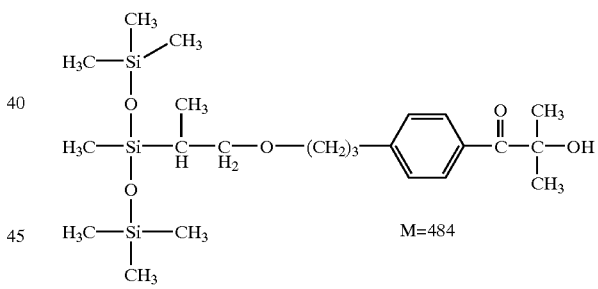

M=484

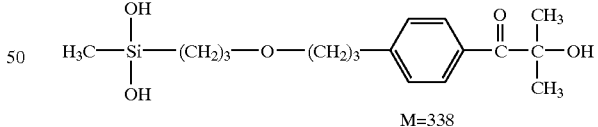

M=338

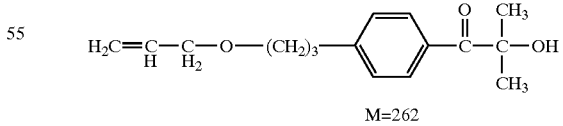

M=262

HO—(CH$_2$)$_3$—〔phenyl〕—C(O)—C(CH$_3$)$_2$—OH

M=222

Example 18

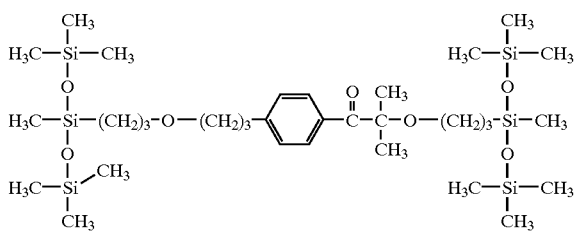

The compound of Example 18 is prepared according to the method described in Example 1, using 1 molar equivalent of 2-allyloxy-1-[4-(3-allyloxy-propyl)-phenyl]-2-methyl-propan-1-one and 2 molar equivalents of 1,1,1,3,5,5,5-heptamethyltrisiloxane.

U.V. ($CH_3CN$) max. at 256 nm ($\epsilon$9542). $^1$H-NMR ($CDCl_3$): 8.14 (m, 2 H, arom.); 7.19 (m, 2 H, arom.); 3.30 (m, 4 H, Ph—$(CH_2)_2$—$CH_2$—O—$CH_2$); 3.14 (m, 2 H, $C(CH_3)_2$—$OCH_2$); 2.65 (m, 2 H, Ph—$CH_2$); 1.82 (m, 2 H, Ph—$(CH_2)_3$—O—$CH_2$—$CH_2$); 1.48 (m, 2 H, $C(CH_3)_2$—$OCH_2$—$CH_2$); 1.42 (s, 6 H, 2 $CH_3$); 1.15 (m, 2H, Ph—$CH_2$—$CH_2$); 0.38 (m, 4 H, 2 $CH_2$—Si); 0.01 (m, 42 H, 14 Si—$CH_3$). m/z (EI and Cl): 746 ($M^+$); according to the MS spectrum, small amounts of compounds 484 ($M^+$); and 238 ($M^+$) are also present. The value M=238 is assigned to a siloxane chain.

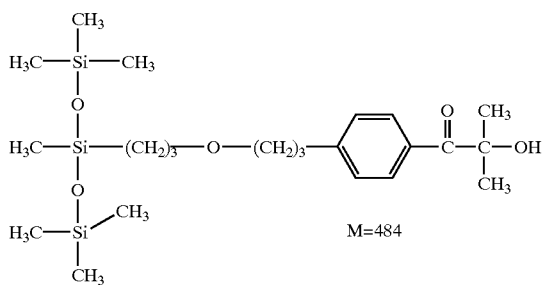

Example 19

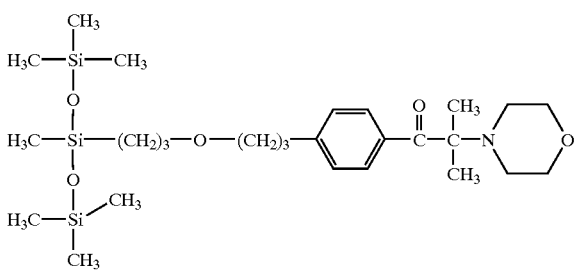

The compound of Example 19 is prepared according to the method described in Example 1, using 1 molar equivalent of 1-[4-(3-allyloxy-propyl)-phenyl]-2-methyl-2-morpholin-4-yl-propan-1-one and 1 molar equivalent of 1,1,1,3,5,5,5-heptamethyltrisiloxane.

U.V. ($CH_3CN$) max. at 253 nm ($\epsilon$14 930). $^1$H-NMR ($CDCl_3$): 8.38 (m, 2 H, arom.); 7.14 (m, 2 H, arom.); 3.60 (m, 4 H, N=$(CH_2$—$CH_2)_2$=O); 3.30 (m, 4 H, Ph—$(CH_2)_2$—$CH_2$—O—$CH_2$); 2.65 (t, 2 H, J=6, Ph—$CH_2$); 2.48 (m, 2 H, N=$(CH_2$—$CH_2)_2$=O); 1.83 (m, 2 H, Ph—$CH_2CH_2$); 1.51 (m, 2 H, Ph—$(CH_2)_3$—O—$CH_2$—$CH_2$); 1.21 (s, 6 H, 2 $CH_3$); 0.38 (m, 2 H, $CH_2$—Si); 0.01 (m, 21 H, 7 Si—$CH_3$). m/z (EI and Cl): 553 ($M^+$); according to the mass spectrum, small amounts of the compounds of 333 ($M^+$); 331 ($M^+$); and 238 ($M^+$) are also still present. The value M=238 is assigned to a siloxane chain.

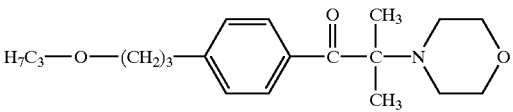

M=333

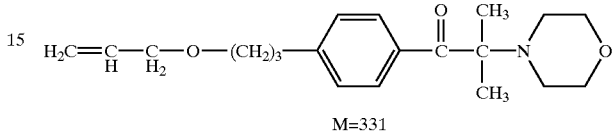

M=331

Example 20

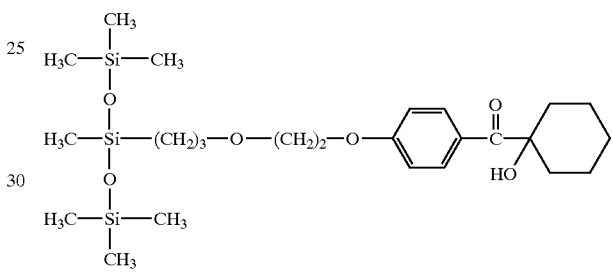

The compound of Example 20 is obtained according to the method described in Example 1, using 1 molar equivalent of [4-(2-allyloxy-ethoxy)-phenyl]-(1-hydroxy-cyclohexyl)-methanone and 1 molar equivalent of 1,1,1,3,5,5,5-heptamethyltrisiloxane.

U.V. ($CH_3CN$) max. at 274 nm ($\epsilon$11 211). $^1$H-NMR ($CDCl_3$): 8.01 (m, 2 H, arom.); 6.87 (m, 2 H, arom.); 4.07 (m, 2 H, Ph—$OCH_2$); 3.71 (m, 2 H, Ph—$O(CH_2)_2$—O—$CH_2$); 3.40 (m, 2 H, Ph—$OCH_2CH_2$); 1.95 (m, 2 H, Ph—O—$(CH_2)_2$—$OCH_2$—$CH_2$); 1.68–1.20 (m, 11 H, —$C_6H_{11}$); 0.38 (m, 2 H, $CH_2$—Si); 0.01 (m, 21 H, 7 Si—$CH_3$). m/z (EI and Cl): 526 ($M^+$); according to the mass spectrum, small amounts of the compounds 304 ($M^+$)(2 signals); 264 ($M^+$) and 238 ($M^+$) are also present. The values M=264 and 238 are assigned to siloxane chains.

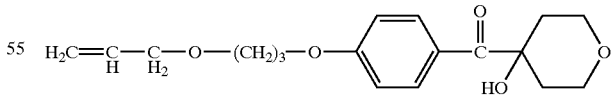

M=304

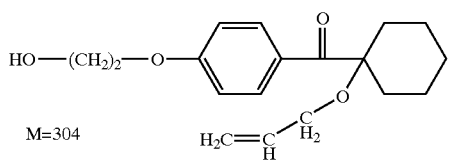

M=304

Example 21
Curing of a UV-curable Clear Lacquer

A UV-curable clear lacquer is prepared by mixing the following components:

- 50.0 parts of a difunctional urethane acrylate ($^{RTM}$Actylan 200, Akcros)
- 25.0 parts tripropylene glycol diacrylate (SR 306, Cray Valley)
- 15.0 parts trimethylolpropane triacrylate (UCB)
- 10.0 parts dipentaerythritol pentaacrylate (SR 399, Cray Valley)

2% of the photoinitiator from Example 1 are added to the mixture. The mixture is applied to a white chipboard panel and is cured using a UV processor below two 80 W/cm lamps at a band speed of 3 m/min. A non-sticky cured film approximately 50 μm thick is obtained. 30 minutes after curing, the pendulum hardness according to König (DIN 53157) is determined in seconds. The higher the value, the greater is the hardness of the crosslinked surface. The static water contact angle (θ) is also determined. For that purpose there is used a Krüss G10 contact angle measuring system. In that procedure, after the formulation has been cured, a drop of water is applied thereto. The contact angle is determined from the equilibrium of forces at the three-phase interface (air/water/coating). A computer program matches the profile of the lying drop of water to a general conic section equation. The differential of the equation at the base line gives the slope at the three-phase contact point and thus the contact angle. The greater the contact angle measured, the better are the moisture-resistance and scratch-resistance of the cured surface. (The following publications give further explanation of the determination of contact angles: "Contact Angle, Wettability, and Adhesion", Advances in Chemistry Series 43, Am. Chem. Soc. 1964; Krüss User Manual, Drop Shape Analysis, Krüss GmbH, Hamburg 1997; G. Hirsch "Bestimmung der Oberflächenspannung von Festkörpern aus Randwinkelmessungen und ihre Bedeutung bei Benetzungsproblemen" Chemie-Ing.-Techn 40.Jahrg. 1968; Volume 13, 639–645.)

The pendulum hardness measured is 130 s; the contact angle θ is 81°.

Example 22
Curing of a UV/thermally Curable System (Dual Cure)

A "Dual-Cure" clear lacquer is prepared by mixing the following components:

- 21.1 parts of a hydroxy-functional polyacrylate ($^{RTM}$Desmophen LS 2009/1, Bayer AG)
- 32.3 parts of a urethane acrylate based on isocyanurate in 80% butyl acetate ($^{RTM}$Roskydal FWO 2518C, Bayer AG)
- 0.3 part flow improver in 10% xylene ($^{RTM}$Baysilone OL 17, Bayer AG)
- 0.3 part flow improver ($^{RTM}$Modaflow, Monsanto)
- 26.0 parts 1-methoxy-2-propanol (Fluka Chemicals)
- 0.5 part flow improver ($^{RTM}$Byk 306, Byk-Chemie)
- 11.2 parts urethane acrylate containing isocyanate groups ($^{RTM}$Roskydal FWO 2545 E, Bayer AG)

To the resulting mixture there are added 2.635% of the photoinitiator from Example 1, 0.375 % bis(2,4,6-trimethylbenzoyl)phenylphosphine oxide ($^{RTM}$Irgacure 819, Ciba Specialty Chemicals), 1.5% of a mixture of 2-[4-[(2-hydroxy-3-dodecyloxypropyl)oxy]-2-hydroxy-phenyl]-4,6-bis(2,4-dimethylphenyl)-1,3,5-triazine and 2-[4-[(2-hydroxy-3-tridecyloxy-propyl)-oxy]-2-hydroxyphenyl]-4,6-bis(2,4-dimethylphenyl)-1,3,5-triazine ($^{RTM}$Tinuvin 400) and 1% of a mixture of bis(1,2,2,6,6-pentamethyl-4-piperidinyl)sebacate and 1-(methyl)-8-(1,2,2,6,6-pentamethyl-4-piperidinyl)-sebacate ($^{RTM}$Tinuvin 292, Ciba Specialty Chemicals). The mixture is applied to a white-coated aluminium sheet, air-dried for 5 minutes at room temperature and heated on a hotplate for 10 minutes at 80° C. The irradiation is carried out thereafter using a UV processor below two 120 W/cm lamps at a band speed of 5 m/min. A non-sticky cured film approximately 40 μm thick is obtained. 45 minutes after curing, the pendulum hardness according to König (DIN 53157) is determined in seconds. The higher the value, the greater is the hardness of the crosslinked surface. The static water contact angle (θ) is also determined, as described in Example 13, using a Krüss G10 contact angle measuring system. The greater the contact angle measured, the better are the moisture-resistance and scratch-resistance of the cured surface. The pendulum hardness measured is 85 s; the contact angle θ is 92°.

Example 23
Siloxane-containing Photoinitiator as Flow Improver

A formulation is prepared by mixing the following components:

- 57.0 parts of a hexa-functional aliphatic urethane acrylate (made by UCB)
- 13.0 parts hexanediol diacrylate (made by UCB)

2% of the compound from Example 13 are dissolved in the formulation. The formulation is then applied using a 100 mm slotted knife to a chipboard panel coated with white primer and the contact angle of the coating relative to water is determined (for a description of contact angle measurement, see Example 21). For that purpose a drop of water of a specific volume is applied to the coated surface and the angle θ of a tangent to the contact surface of the drop relative to the surface is measured using a special lens system and a computer program. The greater the contact angle, the better is the flow of the coating on the substrate in question (in this case a white chipboard panel), that is to say the lower is the surface tension. The contact angle θ for the present formulation is 51.56°.

What is claimed is:

1. A process for the preparation of coatings having scratch-resistant durable surfaces, in which (I) a photocurable formulation which does not contain any siloxane modified resin in addition to the photoinitiator; said photocurable formulation comprising
  (A) an ethylenically unsaturated polymerisable compound; and
  (B) a photoinitiator;
 is prepared;

(II) that formulation is applied to a support; and (III) the formulation is cured either solely by irradiation with electromagnetic radiation of a wavelength of from 200 to 600 nm, or by irradiation with electromagnetic radiation of a wavelength of from 200 to 600 nm and by prior, simultaneous and/or subsequent action of heat;

in which process the formulation comprises as photoinitiator (B) a compound of formula I concentrated at the surface of the formulation, $$\left[ A_1 \underset{\underset{IN}{|}}{\overset{\overset{R_1}{|}}{-Si-O}} \right]_n \left[ \underset{\underset{H}{|}}{\overset{\overset{R_2}{|}}{-Si-O}} \right]_m \left[ \underset{\underset{R_4}{|}}{\overset{\overset{R_3}{|}}{-Si-O}} \right]_p A_2 \right]_x \quad (I)$$

wherein the units of formulae Ia, Ib and/or Ic $$\underset{\underset{IN}{|}}{\overset{\overset{R_1}{|}}{-Si-O-}}, \quad (Ia)$$

$$\underset{\underset{H}{|}}{\overset{\overset{R_2}{|}}{-Si-O-}}, \quad (Ib)$$

$$\underset{\underset{R_4}{|}}{\overset{\overset{R_3}{|}}{-Si-O-}} \quad (Ic)$$

are arranged randomly or in blocks, and wherein
n is a number from 1 to 1000, or, when the siloxane starting material is a mixture of oligomeric siloxanes. n may also be less than 1, but greater than 0;
m is a number from 0 to 100;
p is a number from 0 to 10000;
x is the number 1 or 2;
$A_1$ is $C_1-C_{18}$alkyl or a radical of formula $$-O-\underset{\underset{R_7}{|}}{\overset{\overset{R_5}{|}}{Si}}-R_6;$$

$A_2$ is $C_1-C_{18}$alkyl or a radical of formula $$-\underset{\underset{R_{10}}{|}}{\overset{\overset{R_8}{|}}{Si}}-R_9;$$

or $A_1$ and $A_2$ together are a single bond;
$R_1$, $R_2$, $R_3$, $R_5$, $R_6$, $R_7$, $R_8$, $R_9$ and $R_{10}$ are each independently of the others $C_1-C_{18}$alkyl, phenyl, $C_2-C_6$hydroxyalkyl, $C_2-C_6$aminoalkyl or $C_5-C_8$cycloalkyl;
$R_4$ is $C_1-C18$alkyl; $C_1-C_{18}$alkyl substituted by hydroxy, $C_1-C_{12}$alkoxy, halogen, $C_3-C_8$cycloalkyl and/or by $N(R_{11})(R_{12})$; or $R_4$ is phenyl; phenyl substituted by $C_1-C_{12}$alkyl, $C_1-C_{12}$alkoxy, halogen, hydroxy and/or by $N(R_{11})(R_{12})$; or $R_4$ is $C_5-C_8$cycloalkyl;
$R_{11}$ and $R_{12}$ are each independently of the other hydrogen, $C_1-C_{12}$alkyl or $C_1-C_{12}$hydroxyalkyl, or $R_{11}$ and $R_{12}$ together are $C_2-C_8$alkylene, which may be interrupted by an oxygen atom;

IN when x is 1, is a radical of formula $$-Y-\underset{}{\overset{}{\underset{}{\bigcirc}}}-\overset{O}{\overset{\|}{C}}-\underset{\underset{R_{14}}{|}}{\overset{\overset{R_{13}}{|}}{C}}-X; \text{ or}$$

IN when x is 2, is a radical of formula $$-Y-\underset{}{\overset{}{\underset{}{\bigcirc}}}-\overset{O}{\overset{\|}{C}}-\underset{\underset{R_{14}}{|}}{\overset{\overset{R_{13}}{|}}{C}}-X_1-;$$

$R_{13}$ and $R_{14}$ are each independently of the other $C_1-C_{12}$alkyl, $C_2-C_8$alkenyl, $C_5-C_8$cycloalkyl, phenyl-$C_1-C_3$alkyl; or $R_{13}$ and $R_{14}$ together are $C_2-C_8$alkylene, $C_3-C_9$-oxaalkylene or $C_3-C_9$azaalkylene;
Y is $-(CH_2)_a-$, $-(CH_2)_a-O-$, $-O-(CH_2)_a-O-$, $-(CH_2)_b-O-(CH_2)_a-$, $-(CH_2)_b-O-(CH_2)_a-O-$, $-(CH_2)_2-N(R_{12})-$, $-(CH_2)_b-O-(CH_2)_a-N(R_{12})-$, $-(C_2-C_{10}\text{alkenylene})-O-$, $-(C_2-C_{10}\text{alkenylene})-N(R_{12})-$, $-(C_2-C_{10}\text{alkenylene})-O-(CH_2)_a-O-$ or $-(C_2-C_{10}\text{alkenylene})-O-(CH_2)_a-N(R_{12})-$;
a and b are each independently of the other a number from 0 to 10;
X is $OR_{15}$ or $N(R_{16})(R_{17})$;
$R_{15}$ is hydrogen, $C_1-C_4$alkyl, $C_2-C_8$alkenyl or $C_1-C_4$alkanoyl;
$R_{16}$ and $R_{17}$ are each independently of the other hydrogen, $C_1-C_{12}$alkyl or $C_2-C_6$alkenyl; or $R_{16}$ and $R_{17}$ together are $C_4-C_5$alkylene and, together with the nitrogen atom to which they are bonded, form a 5- or 6-membered ring, which may be interrupted by O or by $N(R_{12})$; and
$X_1$ is a radical $-O-$, $-O-(CH_2)_a-$ or $-N(R_{12})-(CH_2)_a-$.

2. A process according to claim 1, in which the surface-active photoinitiator (B) is a compound of formula I, wherein
n is a number from 1 to 10, or, when the siloxane starting material is a mixture of oligomeric siloxanes, n may also be less than 1, but greater than 0;
m is a number from 0 to 25;
p is a number from 0 to 25;
$A_1$ is $C_1-C_4$alkyl or a radical of formula $$-O-\underset{\underset{R_7}{|}}{\overset{\overset{R_5}{|}}{Si}}-R_6;$$

$A_2$ is $C_1-C_4$alkyl or a radical of formula $$-\underset{\underset{R_{10}}{|}}{\overset{\overset{R_8}{|}}{Si}}-R_9;$$

or $A_1$ and $A_2$ together are a single bond;
$R_1$, $R_2$, $R_3$, $R_5$, $R_6$, $R_7$, $R_8$, $R_9$ and $R_{10}$ are each independently of the others $C_1-C_4$alkyl;

$R_4$ is $C_1$–$C_4$alkyl;

$R_{13}$ and $R_{14}$ are each independently of the other $C_1$–$C_4$alkyl; or $R_{13}$ and $R_{14}$ together are $C_2$–$C_8$alkylene;

Y is —$(CH_2)_a$—O—, —$(CH_2)_b$—O—$(CH_2)_a$— or —$(CH_2)_b$—O—$(CH_2)_a$—O—;

a and b are each independently of the other the number 2 or 3;

$R_{15}$ is hydrogen;

$R_{16}$ and $R_{17}$ together are $C_4$–$C_5$alkylene and together with the nitrogen atom to which they are bonded form a 6-membered ring interrupted by O; and $X_1$ is a radical —O—$(CH_2)_a$—.

3. A process according to claim 1, in which the photocurable formulation comprises as further component at least one thermally crosslinkable compound (C), and the curing of the formulation is carried out by irradiation with electromagnetic radiation of a wavelength of from 200 to 600 nm and by prior, simultaneous and/or subsequent action of heat.

4. A process according to claim 3, wherein the thermally crosslinkable compound (C) is a binder based on a polyacrylate with melamine or on a melamine derivative, or a system based on a polyacrylate polyol and/or polyester polyol with an unblocked polyisocyanate or polyisocyanurate.

5. A process according to claim 1 for the preparation of pigmented and non-pigmented surface-coatings, powder coating compositions, composites and glass fibre cable coatings.

* * * * *